(12) United States Patent
Wenzel et al.

(10) Patent No.: US 9,687,656 B2
(45) Date of Patent: Jun. 27, 2017

(54) ARTERIAL BLOOD PRESSURE MONITORING DEVICES, SYSTEMS AND METHODS FOR USE WHILE PACING

(75) Inventors: Brian Jeffrey Wenzel, San Jose, CA (US); Timothy A. Fayram, Gilroy, CA (US); Allen J. Keel, San Jose, CA (US); Edward Karst, S. Pasadena, CA (US); Wenbo Hou, Lancaster, CA (US); Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1787 days.

(21) Appl. No.: 12/637,574

(22) Filed: Dec. 14, 2009

(65) Prior Publication Data

US 2011/0009755 A1    Jan. 13, 2011

Related U.S. Application Data

(60) Provisional application No. 61/223,992, filed on Jul. 8, 2009.

(51) Int. Cl.
*A61B 5/02* (2006.01)
*A61N 1/365* (2006.01)
(Continued)

(52) U.S. Cl.
CPC ........ *A61N 1/36585* (2013.01); *A61B 5/0215* (2013.01); *A61B 5/0295* (2013.01);
(Continued)

(58) Field of Classification Search
CPC ... A61B 5/0215; A61B 5/0295; A61B 5/1459; B82Y 40/00; B82Y 10/00; G03F 7/0002; A61N 1/36585; A61N 1/08
(Continued)

(56) References Cited

U.S. PATENT DOCUMENTS

| 4,425,920 A | 1/1984 | Bourland |
| 4,676,253 A | 6/1987 | Newman |

(Continued)

FOREIGN PATENT DOCUMENTS

| EP | 0256159 B1 | 5/1991 |
| EP | 0443267 A1 | 8/1991 |
| EP | 0307093 B1 | 12/1995 |

OTHER PUBLICATIONS

25. Impedance Plethysmography—http://www.bem.fi/book/25/25.htm.

(Continued)

*Primary Examiner* — Navin Natnithithadha
*Assistant Examiner* — Eric Messersmith
(74) *Attorney, Agent, or Firm* — Theresa A. Raymer

(57) ABSTRACT

Provided herein are implantable systems, and methods for use therewith, for monitoring a patient's arterial blood pressure while a patient's heart is being paced. A signal (e.g., PPG or IPG signal) indicative of changes in arterial blood volume remote from the patient's heart is obtained using a sensor or electrodes that are implanted remote from the patient's heart. One or more metrics indicative of pulse arrival time (PAT) are determined, where each metric can be determined by determining a time from a paced cardiac event to one or more predetermined features of the signal indicative of changes in arterial blood volume. Based on at the metric(s) indicative of PAT, arterial blood pressure is estimated, which can include determining values indicative of systolic blood pressure, diastolic blood pressure, pulse pressure and/or mean arterial blood pressure, and/or changes in such values.

16 Claims, 12 Drawing Sheets

(51) Int. Cl.
| | | |
|---|---|---|
| *A61B 5/0215* | (2006.01) | |
| *A61B 5/0295* | (2006.01) | |
| *A61B 5/1459* | (2006.01) | |
| *A61N 1/08* | (2006.01) | |
| *G03F 7/00* | (2006.01) | |
| *B82Y 10/00* | (2011.01) | |
| *B82Y 40/00* | (2011.01) | |
| *A61B 5/021* | (2006.01) | |
| *A61B 5/053* | (2006.01) | |
| *A61B 5/00* | (2006.01) | |

(52) U.S. Cl.
CPC ........ *A61B 5/02125* (2013.01); *A61B 5/1459* (2013.01); *A61N 1/08* (2013.01); *B82Y 10/00* (2013.01); *B82Y 40/00* (2013.01); *G03F 7/0002* (2013.01); *A61B 5/0535* (2013.01); *A61B 5/7239* (2013.01)

(58) Field of Classification Search
USPC ............ 600/301, 485, 486, 513; 607/17, 23
See application file for complete search history.

(56) References Cited

U.S. PATENT DOCUMENTS

| | | | |
|---|---|---|---|
| 4,791,931 A | 12/1988 | Slate | |
| 5,113,869 A * | 5/1992 | Nappholz et al. ............ | 600/508 |
| 5,674,256 A | 10/1997 | Carlson | |
| 5,743,267 A * | 4/1998 | Nikolic ................ | A61B 5/0028 |
| | | | 600/485 |
| 5,857,975 A | 1/1999 | Golub | |
| 5,862,805 A | 1/1999 | Nitzan | |
| 5,865,755 A | 2/1999 | Golub | |
| 6,120,459 A | 9/2000 | Nitzan | |
| 6,122,536 A | 9/2000 | Sun | |
| 6,409,675 B1 | 6/2002 | Turcott | |
| 6,575,912 B1 | 6/2003 | Turcott | |
| 6,599,251 B2 | 7/2003 | Chen | |
| 6,616,613 B1 | 9/2003 | Goodman | |
| 6,647,287 B1 | 11/2003 | Peel | |
| 6,648,828 B2 | 11/2003 | Friedman | |
| 6,731,967 B1 | 5/2004 | Turcott | |
| 6,942,622 B1 | 9/2005 | Turcott | |
| 6,997,879 B1 | 2/2006 | Turcott | |
| 7,029,447 B2 | 4/2006 | Rantala | |
| 7,125,383 B2 | 10/2006 | Hoctor | |
| 7,174,203 B2 | 2/2007 | Arand | |
| 7,194,306 B1 | 3/2007 | Turcott | |
| 7,212,861 B1 | 5/2007 | Park | |
| 7,286,875 B1 | 10/2007 | Park | |
| 7,519,422 B2 * | 4/2009 | Lippert et al. .................. | 607/9 |
| 8,010,196 B1 | 8/2011 | Wong et al. | |
| 8,321,017 B2 | 11/2012 | Wenzel et al. | |
| 2002/0001390 A1 | 1/2002 | Kawaguchi | |
| 2002/0151938 A1 | 10/2002 | Corbucci | |
| 2003/0187341 A1 | 10/2003 | Sackner | |
| 2004/0030261 A1 * | 2/2004 | Rantala ................ | A61B 5/0285 |
| | | | 600/561 |
| 2004/0167417 A1 | 8/2004 | Schulhauser et al. | |
| 2005/0131306 A9 | 6/2005 | Mills | |
| 2005/0240233 A1 * | 10/2005 | Lippert et al. .................. | 607/6 |
| 2005/0251059 A1 | 11/2005 | Kim | |
| 2005/0261593 A1 | 11/2005 | Zhang | |
| 2006/0074322 A1 | 4/2006 | Nitzan | |
| 2007/0055163 A1 * | 3/2007 | Asada ................ | A61B 5/02225 |
| | | | 600/485 |
| 2007/0055170 A1 | 3/2007 | Lippert et al. | |
| 2007/0060959 A1 * | 3/2007 | Salo ..................... | A61N 1/3621 |
| | | | 607/6 |
| 2007/0066905 A1 | 3/2007 | Zhang | |
| 2007/0179541 A1 | 8/2007 | Prakash | |
| 2007/0255327 A1 | 11/2007 | Cho | |
| 2007/0276261 A1 | 11/2007 | Banet et al. | |
| 2007/0276632 A1 | 11/2007 | Banet et al. | |
| 2008/0033305 A1 | 2/2008 | Hatib et al. | |
| 2008/0039731 A1 | 2/2008 | McCombie | |
| 2008/0091242 A1 * | 4/2008 | Kamath et al. .................. | 607/6 |
| 2008/0183083 A1 | 7/2008 | Markowitz et al. | |
| 2008/0183232 A1 | 7/2008 | Voss | |
| 2008/0255629 A1 | 10/2008 | Jenson et al. | |
| 2008/0262365 A1 | 10/2008 | Bjorling | |
| 2008/0269624 A1 | 10/2008 | Zhang et al. | |
| 2009/0062667 A1 * | 3/2009 | Fayram ................ | A61B 5/0215 |
| | | | 600/486 |
| 2009/0216132 A1 | 8/2009 | Orbach | |
| 2009/0299203 A1 | 12/2009 | De Voir et al. | |
| 2009/0306732 A1 | 12/2009 | Rosenberg et al. | |
| 2010/0121397 A1 | 5/2010 | Cholette | |
| 2010/0185262 A1 | 7/2010 | Kuhn et al. | |
| 2011/0009457 A1 | 1/2011 | Gorgens et al. | |

OTHER PUBLICATIONS

Stewart et al., "Pseudo-QT Prolongation, Artifactual Electrocardiographic Patterns Produced by Transduction of Cardiovascular Motion," Pacing Clin. Electrophysiol., vol. 6 (Part 1), pp. 940-947 (Sep. 1983).
Allen, "Photoplethysmography and its Application in Clinical Physiological Measurement," Physiol. Meas. 28 (2007) R1-R39.
Chen et al., "Continuous Estimation of Systolic Blood Pressure Using the Pulse Arrival Time and Intermittent Calibration," Medical & Bilogical Engineering & Computing 2000, vol. 38, pp. 569-574.
Turcott et al., "Subcutaneous Photoplethysmography in Extravascular Hemodynamic Sensing," 47 pages.
Turcott et al., "Atria-Ventricular Delay Optimization using Subcutaneous Photoplethysmography," 41 pages.
Payne et al., "Pulse Transit Time Measured from the ECG: An Unreliable Marker of Beat-to-Beat Blood Pressure," American Physiological Society, 2006, pp. 136-141.
Poon et al., "Cuff-less and Noninvasive Measurements of Arterial Blood Pressure by Pulse Transit Time," IEEE 2005, Engineering in Medican and Biology 2ih Annual Conference, pp. 5877-5880.
Sameshima et al., "Continuous Systolic Blood Pressure Monitoring by the Difference in Electrocardiogram and Pulse Oximetry in Near-Term, Exteriorized Goat Fetuses," Journal of the Society for Gynecologic Investigation 2003; 10; 200; 6 pages.
Notice of Allowance mailed Feb. 2, 2012; Related U.S. Appl. No. 12/474,276.
Amendment filed Jan. 3, 2012; Related U.S. Appl. No. 12/474,276.
Terminal Disclaimer flied Jan. 3, 2012; Related U.S. Appl. No. 12/474,276.
Non-Final Office Action mailed Oct. 3, 2011; Related U.S. Appl. No. 12/474,276.
Notice of Allowance mailed Sep. 23, 2011; Related U.S. Appl. No. 11/848,586.
Final Office Action mailed May 28, 2015; Related U.S. Appl. No. 12/637,489.
Amendment filed Jan. 12, 2015; Related U.S. Appl. No. 12/637,489.
Non-Final Office Action mailed Sep. 12, 2014; Related U.S. Appl. No. 12/637,489.
Amendment filed Feb. 5, 2014; Related U.S. Appl. No. 12/637,489.
Non-Final Office Action mailed Sep. 10, 2013; Related U.S. Appl. No. 12/637,489.
Amendment filed May 13, 2013; Related U.S. Appl. No. 12/637,489.
Non-Final Office Action mailed Feb. 13, 2013; Related U.S. Appl. No. 12/637,489.
Non-Final Office Action mailed Dec. 5, 2012; Related U.S. Appl. No. 12/637,489.
Notice of Allowance mailed Aug. 27, 2012; Related U.S. Appl. No. 12/637,596.
Amendment filed Jan. 6, 2012; Related U.S. Appl. No. 12/637,596.
Amendment filed Aug. 15, 2012; Related U.S. Appl. No. 12/637,596.
Non-Final Office Action mailed Oct. 11, 2011; Related U.S. Appl. No. 12/637,596.

(56) References Cited

OTHER PUBLICATIONS

Advisory Action mailed Jan. 20, 2016; Related U.S. Appl. No. 13/662,276.
Amendment filed Dec. 22, 2015; Related U.S. Appl. No. 13/662,276.
Final Office Action mailed Nov. 19, 2015; Related U.S. Appl. No. 13/662,276.
Amendment filed Aug. 6, 2015; Related U.S. Appl. No. 13/662,276.
Non-Final Office Action mailed Jul. 20, 2015; Related U.S. Appl. No. 13/662,276.
Amendment filed Mar. 2, 2015; Related U.S. Appl. No. 13/662,276.
Non-Final Office Action mailed Jan. 16, 2015: Related U.S. Appl. No. 13/662,276.
Preliminary Amendment filed Jul. 30, 2013; Related U.S. Appl. No. 13/662,276.

* cited by examiner

ARTERIAL BLOOD PRESSURE MONITORING DEVICES, SYSTEMS AND METHODS FOR USE WHILE PACING

PRIORITY CLAIM

This application claims priority under 35 U.S.C. 119(e) to U.S. Provisional Patent Application No. 61/223,992, filed Jul. 8, 2009; entitled "Arterial Blood Pressure and Electromechanical Delay (EMD) Monitoring Devices, Systems and Methods", which is incorporated herein by reference.

RELATED APPLICATIONS

This application is related to the following commonly assigned applications, each of which is incorporated herein by reference: U.S. patent application Ser. No. 12/474,276, entitled "Standalone Systemic Arterial Blood Pressure Monitoring Device," filed May 28, 2009, now U.S. Pat. No. 8,162,841; U.S. patent application Ser. No. 11/848,586, entitled "Implantable Systemic Blood Pressure Measurement Systems and Methods," filed Aug. 31, 2007, now U.S. Pat. No. 8,147,416; U.S. patent application Ser. No. 12/637,489, entitled "Arterial Blood Pressure Monitoring Devices, Systems and Methods Using Cadiogenic Impednace Signal," filed the same day as the present application; and U.S. patent application Ser. No. 12/637,596, entitled "Cardiac Electromechanical Delay (EMD) Monitoring Devices, Systems and Methods," filed the same day as the present application, now U.S. Pat. No. 8,321,017.

FIELD OF THE INVENTION

Embodiments of the present invention relate to devices, systems and methods for monitoring arterial blood pressure.

BACKGROUND OF THE INVENTION

A person's circulatory system includes both systemic and pulmonary circulation. Pulmonary circulation supplies the lungs with blood flow, while the systemic circulation takes care of all the other parts of the body. The heart serves as a pump that circulates the blood, while blood vessels act as the conduits that deliver blood to tissue. Both the pulmonary and systemic circulatory systems are made up of arteries, arterioles, capillaries, venules and veins. The arteries take the blood from the heart, while the veins return the blood to the heart Blood pressure is defined as the force exerted by the blood against any unit area of the vessel wall. The measurement unit of blood pressure is millimeters of mercury (mmHg). Pulmonary and systemic arterial blood pressures are pulsatile, having systolic and diastolic blood pressure values. The highest recorded pressure reading in a cardiac cycle is called systolic blood pressure, which results from the active contraction of the ventricle. Although the arterial blood pressure and indeed flow in the arteries is pulsatile, the total volume of blood in the circulation changes little over a cardiac cycle. The lowest arterial pressure reading in a cardiac cycle is called diastolic blood pressure which is maintained by the resistance created by the smaller blood vessels still on the arterial side of the circulatory system (arterioles). Stated another way, the systolic blood pressure is defined as the peak pressure in the arteries, which occurs near the beginning of a cardiac cycle, where a cardiac cycle can be said to begin when blood is ejected from the ventricles. In contrast, the diastolic blood pressure is the lowest pressure, which occurs at the resting phase of the cardiac cycle. The pulse pressure reflects the difference between the maximum and minimum pressures measured (i.e., the difference between the systolic blood pressure and diastolic blood pressure). The mean arterial blood pressure is the average pressure throughout the cardiac cycle.

Arterial pulse pressure, such as mean arterial blood pressure (MAP), is a fundamental clinical parameter used in the assessment of hemodynamic status of a patient. Mean arterial blood pressure can be estimated from real pressure data in a variety of ways. Among the techniques that have been proposed, one is presented below. In this formula, SBP is the systolic blood pressure, and DBP is diastolic blood pressure.

$$MAP = (SBP + 2DBP)/3 = \frac{1}{3}(SBP) + \frac{2}{3}(DBP)$$

Systolic blood pressure and diastolic blood pressure can be obtained in a number of ways. A common approach is to use a stethoscope, an occlusive cuff, and a pressure manometer. However, such an approach is slow, requires the intervention of a skilled clinician and does not provide timely readings as it is a measurement at only a single point in time. While systolic blood pressure and diastolic blood pressure can also be obtained in more automated fashions, it is not always practical to obtain measures of pressure using a cuff and pressure transducer combination, especially if the intention or desire is to monitor systemic arterial blood pressure on a chronic basis.

Another approach for obtaining measures of arterial blood pressure is to use an intravascular pressure transducer. However, an intravascular device may cause problems, such as, embolization, nerve damage, infection, bleeding and/or vessel wall damage. Additionally, the implantation of an intravascular lead requires a highly skilled physician such as a surgeon, electrophysiologist, or interventional cardiologist.

Plethysmography, the measurement of volume of an organ or body part, has a history that extends over 100 years . Photoplethysmography (PPG) uses optical techniques to perform volume measurements, and was first described in the 1930s. While best known for their role in pulse oximetry, PPG sensors have also been used to indirectly measure blood pressure. For example, non-invasive PPG sensors have been used in combination with an inflatable cuff in a device known as Finapres. U.S. Pat. No. 4,406,289 (Wesseling et al.) and U.S. Pat. No. 4,475,940 (Hyndman) are exemplary patents that relate to the Finapres technique. The cuff is applied to a patient's finger, and the PPG sensor measures the absorption at a wavelength specific for hemoglobin. After the cuff is used to measure the individual's mean arterial blood pressure, the cuff pressure around the finger is then varied to maintain the transmural pressure at a constant predetermined pressure as determined by the PPG sensor. The Finapres device tracks the intra-arterial blood pressure wave by adjusting the cuff pressure to maintain the optical absorption constant at all times.

There are a number of disadvantages to the Finapres technique. For example, when there exists peripheral vasoconstriction, poor vascular circulation, or other factors, the blood pressure measured in a finger is not necessarily representative of central blood pressure. Further, maintaining continuous cuff pressure causes restriction of the circulation in the finger being used, which is uncomfortable when maintained for extended periods of time. Accordingly, the Finapres technique is not practical for chronic use. Additionally, because of the need for a pneumatic cuff, a Finapres device can not be used as an implanted sensor.

Simple external blood pressure monitors also exist, but they do not offer continuous measurement and data logging capability. These devices can be purchased at a drug store, but patient compliance is required to make regular measurements and accurately record the data. Additionally, portable external miniature monitors that automatically log blood pressure data exist, but these devices can only store a day or so of data and require clinician interaction to download and process the measured data.

As is evident from the above description, there is the need for improved systems and methods for monitoring arterial blood pressure, including systolic blood pressure, diastolic blood pressure and mean arterial blood pressure.

Electromechanical delay (EMD) is the time delay between onset of ventricular electrical activation and mechanical ejection of blood from the heart. This delay is partly due to the time required for the contractile elements of muscles to stretch the series elastic components. EMD is believed to be affected by conduction abnormalities, myocardial contractility and cardiac diseases, including but not limited to heart failure (HF), mitral stenosis, and hypertension. Accordingly, monitoring EMD can be useful for monitoring conduction abnormalities, myocardial contractility and cardiac diseases.

SUMMARY

Certain embodiments of the present invention related implantable systems, and methods for use therewith, for monitoring a patient's systemic arterial blood pressure. One or more electrodes implanted within and/or on the patient's heart are used to obtain a cardiogenic impedance (CI) signal indicative of cardiac contractile activity. Additionally, an implanted sensor or implanted electrodes, remote from the patient's heart, are used to obtain a signal indicative of changes in arterial blood volume remote from the patient's heart. In an embodiment, an implanted photoplethysmography sensor, remote from the patient's heart, is used to obtain a photoplethysmography (PPG) signal indicative of changes in arterial blood volume remote from the patient's heart. In an alternative embodiment, implanted electrodes, remote from the patient's heart, are used to obtain an impedance plethysmography signal (IPG) indicative of changes in arterial blood volume remote from the patient's heart. Other sensors remote from the patient's heart can alternatively be used to obtain other signals indicative of changes in arterial blood volume remote from the patient's heart.

In certain embodiments, one or more predetermined features of the CI signal are detected, as are one or more predetermined features of the signal indicative of changes in arterial blood volume remote from the patient's heart. Exemplary predetermined features of the CI signal that can be detected include, but are not limited to, minimum amplitude of the CI signal, maximum upward slope of the CI signal, maximum amplitude of the CI signal and maximum downward slope of the CI signal. Presuming the signal indicative of changes in arterial blood volume is a PPG or IPG signal, exemplary predetermined features that can be detected include, but are not limited to, minimum amplitude of the PPG or IPG signal, maximum upward slope of the PPG or IPG signal, maximum amplitude of the PPG or IPG signal, dicrotic notch of the PPG signal or IPG, maximum downward slope of the PPG or IPG signal prior to the dicrotic notch, and maximum downward slope of the PPG or IPG signal following the dicrotic notch.

In certain embodiments, one or more metrics indicative of pulse arrival time (PAT) are determined, where each metric indicative of PAT is determined by determining a time from one of the detected features of the CI signal to one of the detected features of the signal indicative of changes in arterial blood volume. Based on at least one of the metric(s) indicative of PAT, the patient's arterial blood pressure is estimated. This can include determining values indicative of systolic blood pressure (SBP), diastolic blood pressure (DBP), pulse pressure (PP) and/or mean arterial blood pressure (MAP), and/or changes in such values.

The above described techniques for monitoring a patient's arterial blood pressure can be performed while a patient's heart is beating intrinsically, or while the patient's heart is being paced with a voltage sufficient to cause capture.

In accordance with further embodiments of the present invention, where the patient's arterial blood pressure is being monitored while the patient's heart is being paced, one or more metrics indicative of pulse arrival time (PAT) can alternatively be determined by determining a time from a paced cardiac event to one or more predetermined features of the signal (e.g., PPG or IPG signal) indicative of changes in arterial blood volume. In such embodiments, these alternative metrics indicative of PAT can be used to estimate the patient's arterial blood pressure.

In certain embodiments, a patient's electromechanical delay (EMD) can be monitored. More specifically, one or more values indicative EMD, between delivery of pacing and a mechanical cardiac contraction resulting from the pacing, can be determined. In such embodiments, metric(s) indicative of PAT can also be determined based on the value(s) indicative of EMD. For example, a metric indicative of PAT can be determined by determining a time from a paced cardiac event to a predetermined feature of the signal indicative of changes in arterial blood volume, minus the determined value indicative of EMD. Determined values indicative of EMD may also be used as feedback to adjust pacing, e.g., to minimize variance of a value indicative of electromechanical delay (EMD).

In specific embodiments, paced cardiac events are caused by delivering sufficient pacing stimulation to cause capture of the patient's heart. Using one or more electrodes implanted within and/or on the patient's heart, a CI signal indicative of cardiac contractile activity while the patient's heart is being paced is obtained. One or more predetermined features of the obtained CI signal is/are detected. One or more values indicative of the patient's EMD can be determined by determining a time between a delivered pacing stimulation and at least one of the one or more detected features of the CI signal.

Additional and alternative embodiments, features and advantages of the invention will appear from the following description in which the preferred embodiments have been set forth in detail, in conjunction with the accompanying drawings and claims.

DETAILED DESCRIPTION OF THE INVENTION

Figure 1A:
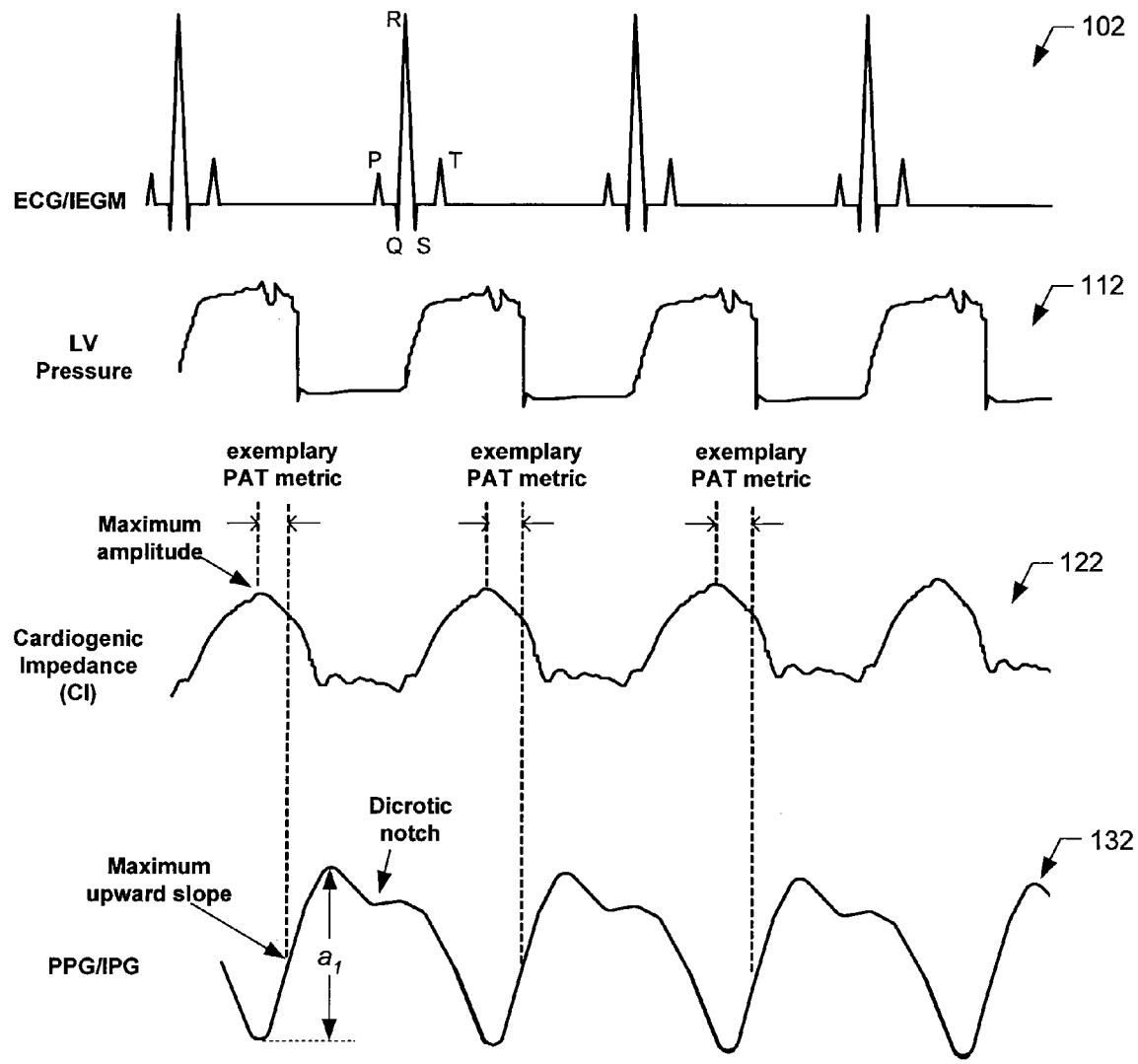
FIG. 1A includes exemplary signal waveforms that are used to show the relative timing of various signals, and how an exemplary pulse arrival time (PAT) metric can be determined in accordance with an embodiment of the present invention. The waveforms include an IEGM/ECG signal, a left ventricular pressure signal, a CI signal and a PPG/IPG signal.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art that the present invention, as described below, may be implemented in many different embodiments of hardware, software, firmware, and/or the entities illustrated in the figures. Any actual software, firmware and/or hardware described herein is not limiting of the present invention. Thus, the operation and behavior of the present invention will be described with the understanding that modifications and variations of the embodiments are possible, given the level of detail presented herein.

Referring to FIG. 1A, the representative signal waveforms therein are used to show the relative timing of electrical and mechanical cardiac events that occur during cardiac cycles. The upper most waveform is representative of an electrocardiogram (ECG) or intracardiac electrogram (IEGM) signal 102 (collectively referred to as ECG/IEGM signal 102), which is indicative of electrical activity of the patient' heart. The following waveform is representative of a left ventricular (LV) pressure signal 112. The next waveform is representative of a cardiogenic impedance (CI) signal 122, which is an impedance measurement that has been inverted to reflect blood volume in the heart and aorta. The last waveform is representative of a photoplethysmography (PPG) signal or impedance plethysmography signal (IPG) 132, both of which are indicative of changes in arterial blood volume remote from the patient's heart. Signals 112, 122 and 132 are all indicative of mechanical activity of a patient's heart. For example, the PPG or IPG signal 132 (collectively referred to as PPG/IPG signal 132) is indicative of mechanical activity of the patient's heart because the PPG/IPG signal 132 represents changes in the flow of blood through the vessels probed by the PPG/IPG sensor (or stated another way, changes in arterial blood volume), which is dependent on the mechanical activity of the heart.

Referring to the ECG/IEGM signal 102, each cycle of the signal 102 is shown as including a P wave, a QRS complex (including Q, R and S waves) and a T wave. The P wave is caused by depolarization of the atria. This is followed by atrial contraction, during which expulsion of blood from the atrium results in further filling of the ventricle. Ventricular depolarization, indicated by the QRS complex, initiates contraction of the ventricles resulting in a rise in ventricular pressure until it exceeds the pulmonary and aortic diastolic blood pressures to result in forward flow as the blood is ejected from the ventricles. Ventricular repolarization occurs thereafter, as indicated by the T wave and this is associated with the onset of ventricular relaxation in which forward flow stops from the ventricles into the aorta and pulmonary arteries. Thereafter, the pressure in the ventricles falls below that in the atria at which time the mitral and tricuspid valves open to begin to passively fill the ventricles during diastole.

Figure 1B:
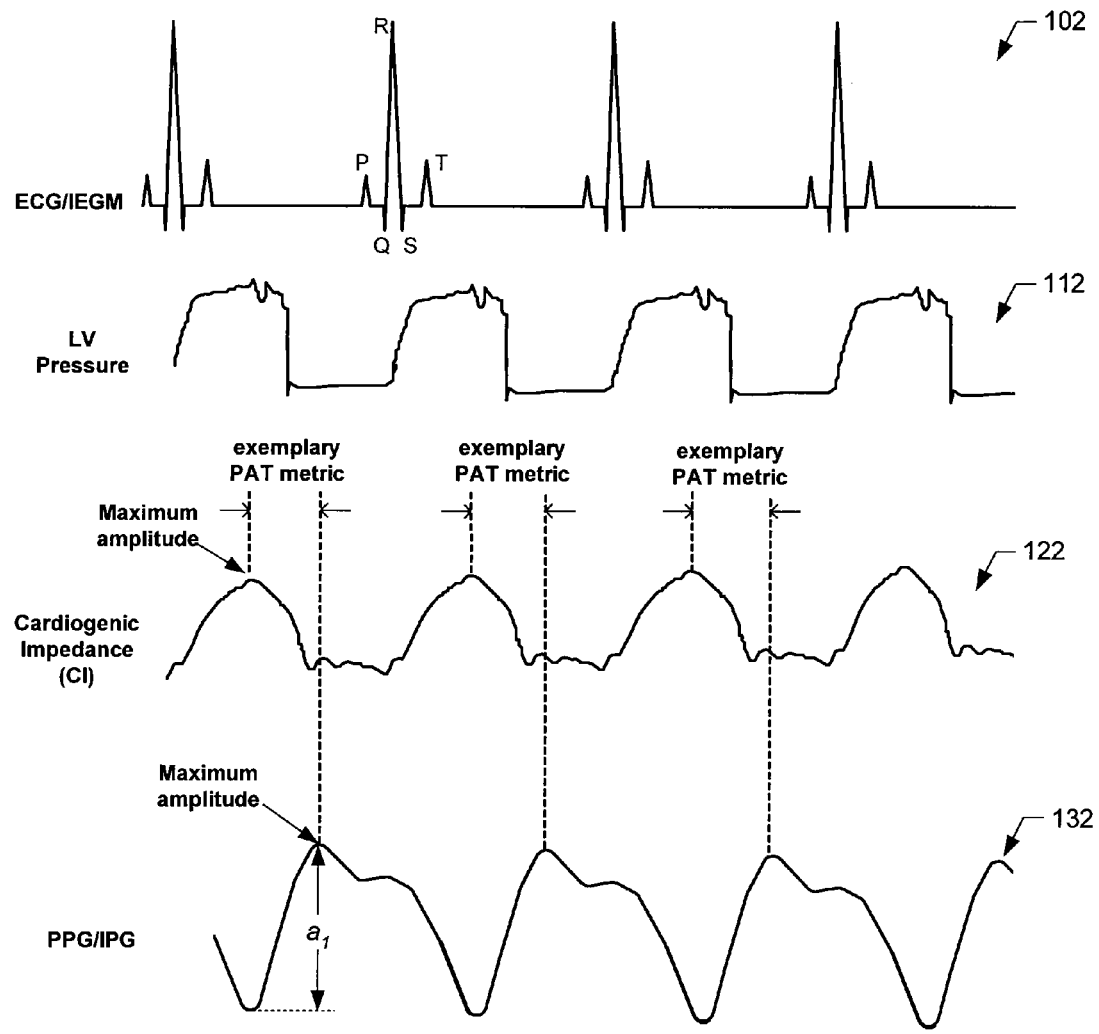
FIG. 1B includes the same exemplary signal waveforms shown in FIG. 1A, but shows how another exemplary PAT metric can be determined in accordance with an embodiment of the present invention.

An exemplary metric indicative of pulse arrival time, which can be used to determine to estimate a patient's blood pressure, is also shown in FIG. 1A. In general, a metric indicative of pulse arrival time (PAT) can be determined, in accordance with embodiments of the present invention, by determining a time from a detected predetermined feature of a CI signal (e.g., 122) to a detected predetermined feature of the signal indicative of changes in arterial volume, which can be a PPG or IPG signal (e.g., 132), but is not limited thereto. In FIG. 1A, the predetermined feature of the CI signal is the maximum amplitude, and the predetermined feature of the PPG/IPG signal is the maximum upward slope. In other words, the metric indicative of PAT can be determined by determining a time from the maximum amplitude of the CI signal 122 to the maximum upward slope of the PPG/IPG signal 132, as illustrated in FIG. 1A. Alternatively, as illustrated in FIG. 1B, the metric indicative of PAT can be determined by determining a time from the maximum upward slope of the CI signal 122 to the maximum downward slope of the PPG/IPG signal 132. These are just a few examples, which are not meant to be limiting. Alternative predetermined features of the CI signal can be used, as can alternative predetermined features of the PPG/IPG signal. Examples of other features of the CI signal and the PPG/IPG signal are discussed below.

Figure 1C:
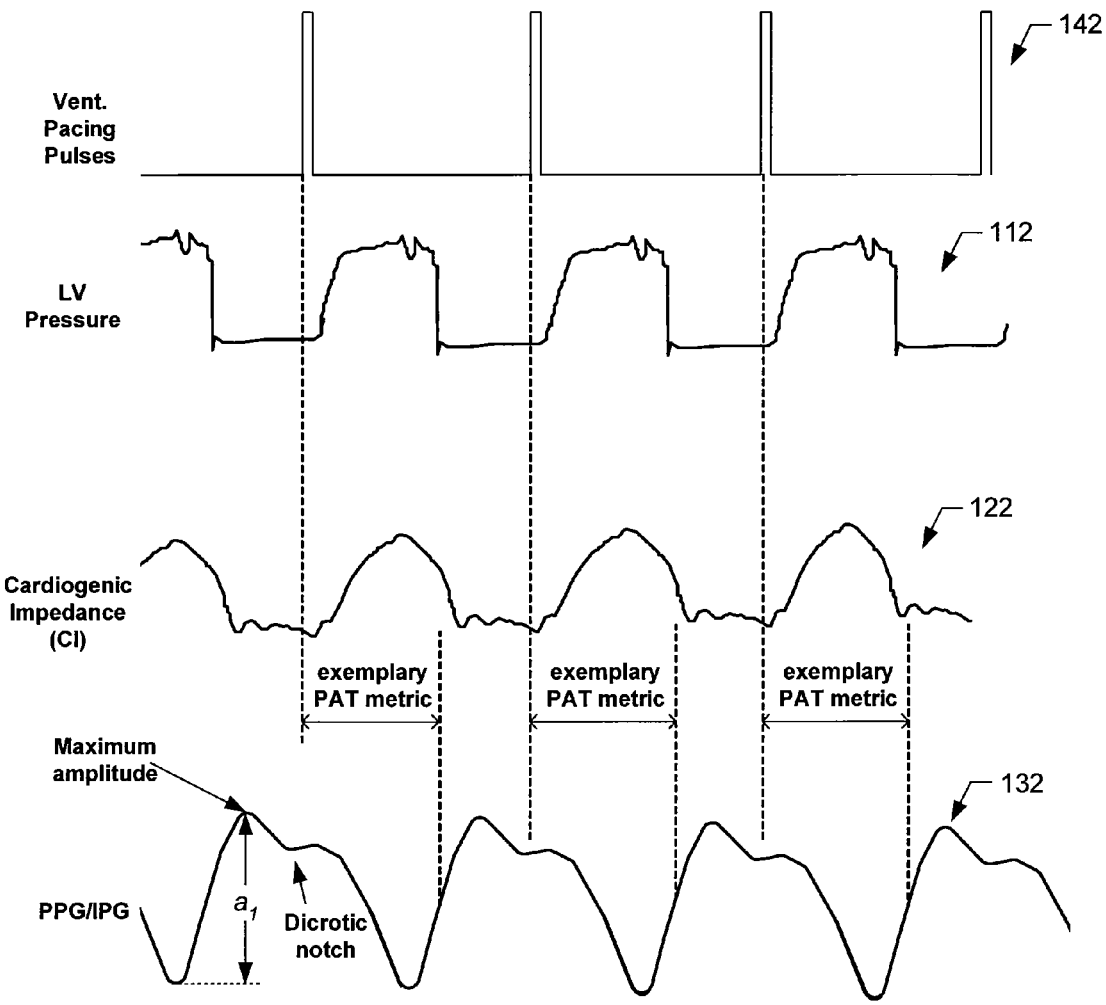
FIG. 1C is similar to FIG. 1A, but the IEGM/ECG signal is replaced with a ventricular pacing signal, and shows how still another exemplary PAT metric can be determined in accordance with an embodiment of the present invention.

Referring now to FIG. 1C, the top most waveform illustrates a ventricular pacing signal 142 that is used to pace a patient's heart. As illustrated in FIG. 1C, where ventricular pacing pulses are being used to pace a patient's heart, the metric indicative of PAT can be determined by determining a time from a ventricular pacing pulse to a maximum upward slope (or some other predetermined feature, e.g., the maximum amplitude, the dicrotic notch) of the PPG/IPG signal 132.

Figure 2A:
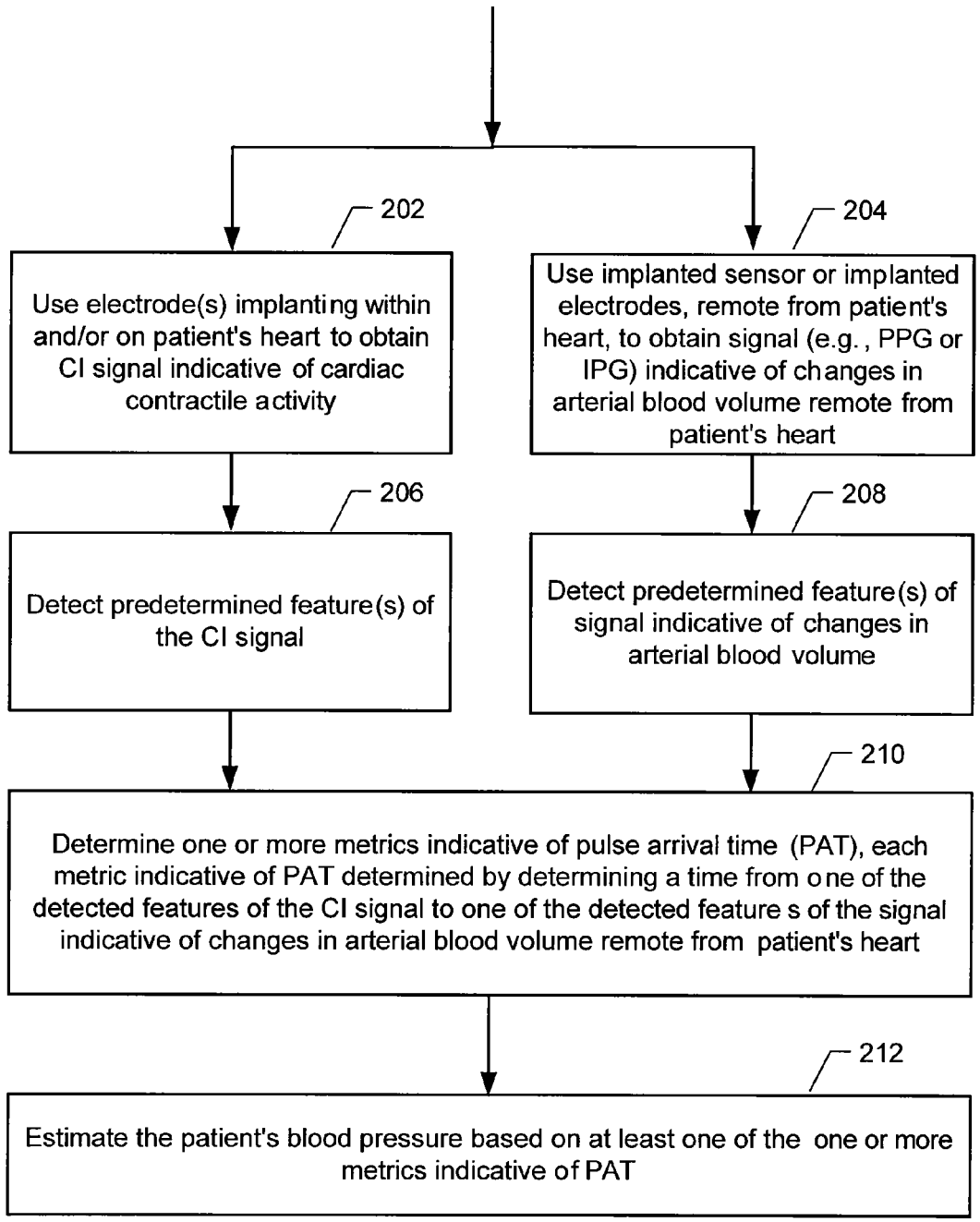
FIG. 2A is a high level flow diagram that is used to explain various embodiments of the present invention that can be used to estimate a patient's blood pressure.

The high level flow diagram of FIG. 2A will now be used to explain various embodiments of the present invention that can be used to estimate a patient's arterial blood pressure. Such embodiments can be implemented by an implantable system, examples of which are discussed below with reference to FIGS. 3 and 4. In FIG. 2A and the other flow diagrams described herein, the various algorithmic steps are summarized in individual 'blocks'. Such blocks describe specific actions or decisions that are made or carried out as the algorithm proceeds. Where a microcontroller (or equivalent) is employed, the flow diagram presented herein provides the basis for a 'control program' that may be used by such a microcontroller (or equivalent) to effectuate the desired control of the implantable system. Those skilled in the art may readily write such a control program based on the flow diagram and other descriptions presented herein.

Referring to FIG. 2A, at steps 202 and 204, one or more electrodes implanted within and/or on the patient's heart is/are used to obtain a cardiogenic impedance (CI) signal indicative of cardiac contractile activity, and an implanted sensor (e.g., optical sensor) or implanted electrodes remote from the patient's heart is used to obtain a signal indicative of changes in arterial blood volume. The signal indicative of changes in arterial blood volume obtained at step 204 can be a PPG signal, an IPG signal, or some other plethysmography signal. An optical sensor can be used to obtain a PPG signal, or implanted electrodes can be used to obtain an IPG signal.

Examples of electrodes and circuitry that can be used to obtain a CI signal are discussed below with reference to FIG. 3-5. In certain embodiments, multiple CI vectors can be recorded simultaneously, and such multiple CI vectors can be combined to provide the CI signal obtained as step 202. Such embodiments may increase the accuracy of the cardiac cycle reference point determined at step 206, discussed below.

Exemplary sensors that can be used to obtain a PPG signal are discussed below with reference to FIGS. 3 and 4. Exemplary sensors (which can include electrodes and circuitry) that can be used to obtain an IPG signal are also discussed below. In still other embodiments, the plethysmography signal indicative of changes in arterial blood volume can be a signal output by a sensor including a piezo-electric diaphragm. Alternative sensors that can be used to produce the plethysmography signal indicative of changes in arterial blood volume, include, but are not limited to, a close range microphone, a sensor including a small mass on the end of a piezo bending beam with the mass located on the surface of a small artery, a transmission mode infrared motion sensor sensing across the surface of a small artery, or a MEMS accelerometer located on the surface of a small artery. Such alternative sensors can be located, e.g., on the tip of a short lead connected to a device that is subcutaneously implanted. The implanted sensor is preferably extravascular, and preferably a sufficient distance from the patient's heart such that meaningful changes in the amount of time it takes a pulse wave originating in the heart to reach the implanted sensor can be detected, thereby enabling changes in arterial blood pressure to be detected. For example, it is preferred that the implanted sensor (used to obtain the signal indicative of changes in arterial blood volume) is at least 10 mm from the patient's aortic root. Such a sensor can be implanted, e.g., in the pectoral region of a patient. An alternative location for implantation of the sensor includes, but is not limited to, the patient's abdominal region. For the remainder of this discussion, it will be assumed that the signal obtained at step 204 is a PPG or IPG signal, which are collectively referred to as a PPG/IPG signal. However, as just explained above, alternative plethysmography signals can be used.

Still referring to FIG. 2A, at steps 206 and 208, one or more predetermined features of the CI signal is/are detected, and one or more predetermined features of the signal indicative of changes in arterial blood volume (e.g., the PPG/IPG signal) is/are detected. The predetermined feature(s) of the CI signal, detected at step 206, can be the minimum amplitude of the CI signal, the maximum upward slope of the CI signal, the maximum amplitude of the CI signal, and/or the maximum downward slope of the CI signal, but is not limited thereto. The predetermined feature(s) of the PPG/IPG signal, detected at step 208, can be the minimum amplitude of the PPG/IPG signal, the maximum upward slope of the PPG/IPG signal, the maximum amplitude of the PPG/IPG signal, the dicrotic notch of the PPG/IPG signal, the maximum downward slope of the PPG/IPG signal prior to the dicrotic notch, and/or the maximum downward slope of the PPG/IPG signal after the dicrotic notch, but is not limited thereto.

At step 210, one or more metrics indicative of pulse arrival time (PAT) is/are determined, where each metric indicative of PAT is determined by determining a time from one of the detected features of the CI signal to one of the detected features of the signal (e.g., PPG/IPG signal) indicative of changes in arterial blood volume remote from the patient's heart. Exemplary metrics indicative of PAT that can be determined at step 210 were discussed above with reference to FIGS. 1A and 1B, but embodiments of the present invention are not limited to such examples.

At step 212, the patient's arterial blood pressure is estimated based on at least one determined metric indicative of PAT. Various arterial blood pressure measurements can be estimated, including systolic blood pressure (SBP), diastolic blood pressure (DBP), pulse pressure (PP) and/or mean arterial blood pressure (MAP). The SBP is the peak pressure in the arteries, which occurs near the beginning of a cardiac cycle. The DBP is the lowest pressure in the arteries, which occurs at the end of the diastolic phase of the arterial circulation. This corresponds to the end of the filling phase of the cardiac cycle with respect to ventricular function. The PP is the difference between the systolic and diastolic blood pressures. The MAP is a weighted average of arterial blood pressure throughout the cardiac cycle.

Because implanted electrodes, and in certain embodiments an implanted sensor, are used to obtain the various arterial blood pressure estimates, a patient's arterial blood pressure can be monitored on a chronic basis. Thus, arterial blood pressure can be tracked to monitor a patient's evolving cardiac disease state, and to trigger alerts (e.g., in response to which a patient may take blood pressure medication). Additionally, arterial blood pressure measurements can be used as a measure of a patient's hemodynamic function.

Embodiments of the present invention use the concept of pulse arrival time (PAT), also known as pulse transmit time (PTT), or pulse wave velocity (PWV) to monitor arterial blood pressure. However, embodiments of the present invention differ from prior art non-implanted systems that rely on pulse arrival time. For example, most such prior art systems are not practical for chronic use. Further, unlike prior art systems, specific embodiments of the present invention utilize a CI signal to determine PATs, which is believed to be advantageous because the CI signal is not affected by variations in pre-ejection periods that result from changes in electromechanical coupling, heart failure and/or mitral valve regurgitation. Thus, use of a CI signal to determine metrics indicative of PAT may be superior to techniques that rely on an IEGM or ECG signal to determine PATs, since during periods of heart failure and mitral valve regurgitation the variations in pre-ejection periods can affect IEGM and ECG signals in a manner that may reduce that accuracy of blood pressure estimates based thereon.

In accordance with certain embodiments, at step 212, one or more values indicative of SBP, DBP, PP and/or MAP is/are determined based on one or more metrics indicative of PAT (each also referred to as a "PAT metric"), using an equation, model, lookup table, or the like. Some exemplary equations and models that can be used to estimate such arterial blood pressure measurements are discussed below.

PAT generally has a negative correlation with SBP, in that the greater the PAT the lower the SBP, and the lower the PAT the greater the SBP. In a simplest embodiment based on a linear approximation, the equation SBP≈1/(PAT metric) can be used to estimate SBP. In another embodiment, one or more patient specific correlation factor (e.g., a constant K) is used when estimating SBP at step 212. For example, the equation SBP≈K/(PAT metric) can be used to estimate SBP at step 212, where K is a patient specific correlation factor determined during a calibration procedure, an example of which is discussed below. Non-linear approximations can also be used to estimate SBP, e.g., SBP≈K/(PAT metric)$^2$, or SBP≈K1/(PAT metric)$^2$+K2/(PAT metric), with K, or K1 and K2 being patient specific correlation factor(s) determined during a calibration procedure. Alternative equations could be SBP≈K/(PAT metric)+β, SBP≈K/(PAT metric)$^2$+β, or SBP≈K1/(PAT metric)$^2$+K2/(PAT metric) +β. These are just a few exemplary equations that can be used to estimate SBP, which are not meant to be limiting. Similar equations can be provided for estimating DBP, PP and/or MAP based on PAT metrics. In certain embodiments, one or more look-up table, which may be calibrated for a patient, can be used to estimate arterial blood pressure based on one or more PAT metric.

Multiple different metrics indicative of PAT can be determined, and used in an equation to estimate one or more values indicative of SBP, DBP, PP and/or MAP. Metrics indicative of morphological features of the PPG or IPG signal indicative of the changes in arterial blood volume, such as area under the curve, peak-to-peak amplitude ($a_1$ shown in FIGS. 1A and 1B) and/or full width at half max (FWHM) of a PPG or IPG signal can also be used in such equations. For example, the equation SBP≈K/(PAT metric)+β*(peak-to-peak amplitude of PPG/IPG curve) can be used, with K and β being patient specific correlation factors determined during a calibration procedure. One of ordinary skill in the art reading this disclosure would realize that various alternative linear or non-linear equations can be used to estimate SBP, DBP, PP and/or MAP that are within the scope of the present invention. Such equations can be based on one or more metrics indicative of PAT, and optionally also based on one or more metrics indicative of morphological features of the signal indicative of changes in arterial blood volume.

In specific embodiments, a regression model and/or other mathematical models and equations can be used to estimate SBP, DBP, PP and/or MAP, using one or more metrics indicative of PAT, optionally one or more metrics indicative of morphological features of the signal indicative of changes in arterial blood volume, as well as actual measures of SBP, DBP, PP and/or MAP obtained during a calibration procedure. For example, a blood pressure estimation model can combine one or more PAT metrics and one or more morphological features. Such models can include nonlinear terms, such as polynomial or exponential factors. In one embodiment, a model uses multiple linear regression to estimate blood pressure. A model may also use partial least squares or principal components analysis. Such models can be calibrated using one or more reference blood pressure measurements, some examples of which are discussed below. Thereafter, as a patient's arterial blood pressure evolves over time, changes in PAT metrics and optionally also morphological features (e.g., peak-to-peak amplitude) derived from a plethysmography signal are used to update the estimates of arterial blood pressure.

Where multiple metrics indicative of PAT are determined, such metrics can be combined, e.g., by determining a simple or weighted average of the metrics. Alternatively, multiple metrics indicative of PAT can be used in the equations or models used to estimate SBP, DBP, PP and/or MAP. For example, DBP can be estimated using the equation DBP≈K1/(time from max amplitude of CI signal to max upward slope of PPG or IPG signal)−K2/(time from max amplitude of CI signal to max downward slope of PPG or IPG signal)+β. In this equation, one metric indicative of PAT is the time from max amplitude of CI signal to max upward slope of PPG or IPG signal, and another metric indicative of PAT is the time from max amplitude of CI signal to max downward slope of PPG or IPG signal.

PP can be can be determined by determining the difference between SBP and DBP, and MAP can be determined by determining a weighted average of SBP and DBP (e.g., MAP=⅓SBP+⅔DBP). Alternatively, one or more equations, models or tables can be used to estimate PP and/or MAP based on one or more of the various metrics indicative of PAT described above, without first estimating SBP and/or DBP.

An exemplary calibration procedure (performed at implant and/or thereafter) will now be explained. During the calibration procedure, actual measures of arterial blood pressure (including SBP, DBP, PP and/or MAP) are measured using any known accurate acute technique, and one or more metric indicative of PAT (i.e., PAT metric(s)) are measured in a manner described above using an implanted device. Optionally, metrics indicative of morphological features of the signal indicative of changes in arterial blood volume, such as a peak-to-peak amplitude $a_1$ of the PPG/IPG signal, can also be determined by the implanted device. The actual measure(s) of the patient's SBP, DBP, PP and/or MAP can be obtained, e.g., using a non-invasive auscultatory or oscillometric techniques, or an invasive intravascular cannula method, or any other acute technique. For a more specific example, actual arterial blood pressure measurements (e.g., SBP and DBP) can be measured using a high fidelity micrometer-tipped pressure catheter (e.g., model 4F, SPC-120, available from Millar Instruments, Tex.), which is placed in the ascending aorta via a carotid arteriotomy.

Based on the actual measures of arterial blood pressure, and the metrics indicative of PAT determined using the techniques described above (and optionally also metrics indicative of morphological features of the signal indicative of changes in arterial blood volume, such as a peak-to-peak amplitude $a_1$ of the PPG/IPG signal), various patient specific correlation factors (e.g., K and β) can be calculated by an external programmer, or the like, e.g., using regression models and/or linear or non-linear equations. The patient could also be asked to exercise, or could be appropriately paced, to change the patient's arterial blood pressure, to thereby check the accuracy of the patient correlation factor(s) over a range of SBPs, DBPs, PPs and/or MAPs and PAT metrics. If appropriate, the patient correlation factor(s) can be adjusted so that such factor(s) is/are accurate over a range of systolic blood pressures. Presuming a metric indicative of PAT is measured in msec, the units of the patient specific correlation factor(s) can be, e.g., mmHg·msec or mmHg·msec$^2$, so that when multiplied by 1/(PAT metric) or 1/(PAT metric)$^2$, the resulting estimate of arterial blood pressure has units of mmHg. Use of alternative linear and non-linear equations, look up tables and interpolation are also within the scope of the present invention. After appropriate equations, models and/or look-up tables and one or more patient specific correlations factors (determined during calibration) are programmed into an implanted device, the implanted device can determine estimates of arterial blood pressure (e.g., SBP, DBP, PP and/or MAP) in real time based on one or more PAT metrics as determined by the implanted device in real time.

In some embodiments, an IEGM signal can also be obtained, along the CI signal obtained at step 202 and the signal indicative of changes in arterial blood volume obtained at step 204. In such embodiments, by detecting R-waves of the IEGM signal (in any well known manner), R-wave markers can be used to increase the accuracy of detecting the pre-determined feature(s) of the CI signal at step 206. For example, if it is known that the maximum of the CI signal should occur within a certain window that will typically occur between X and Y msec following an R-wave, then the maximum of the CI signal may only be looked for during that window. Such use of an IEGM signal may increase the accuracy of arterial blood pressure estimates.

Figure 2B:
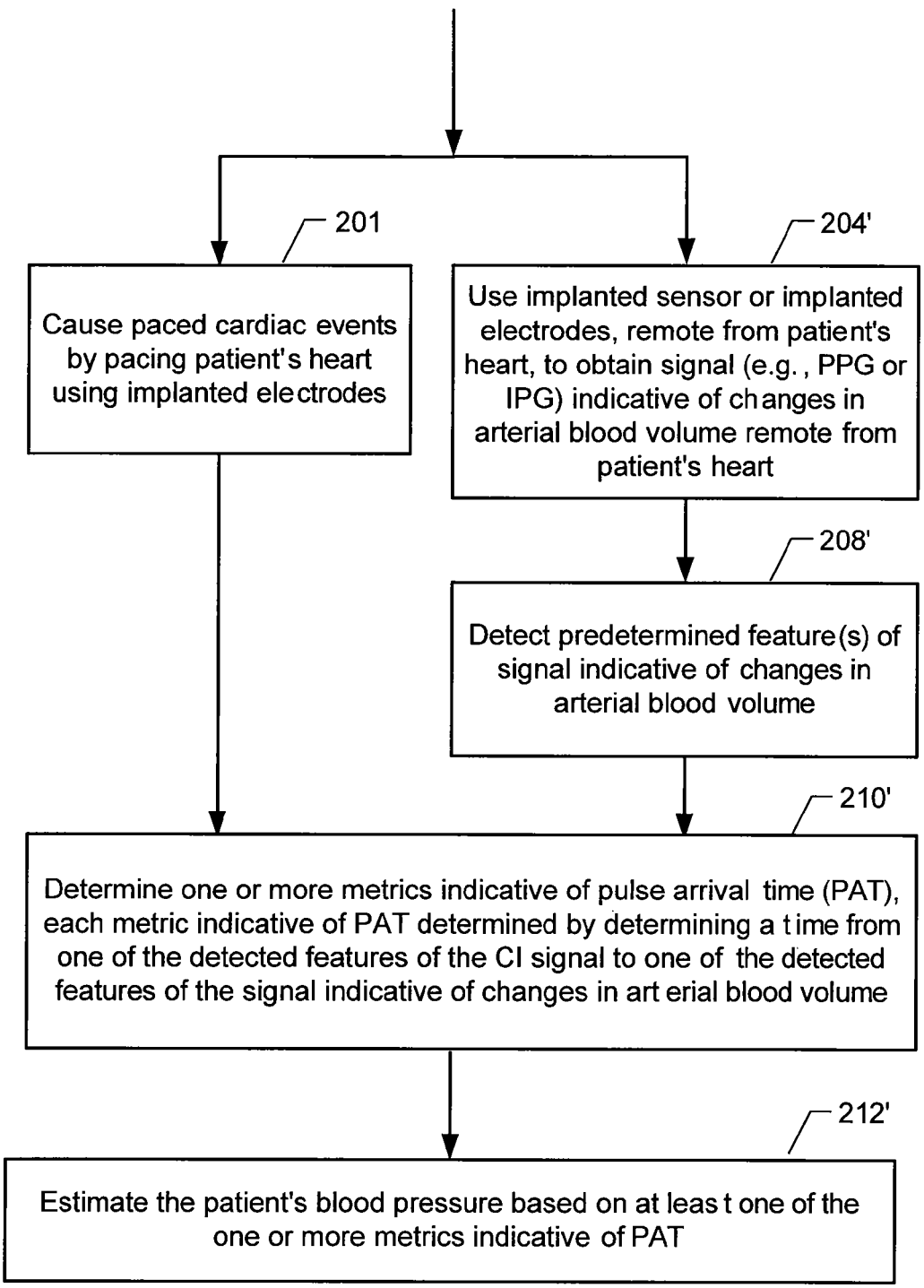
FIG. 2B is a high level flow diagram that is used to explain alternative embodiments of the present invention that can be used to estimate a patient's blood pressure.

Alternative embodiments of the present invention, for monitoring a patient's arterial blood pressure, will now be described with reference to the high level flow diagram of FIG. 2B. The embodiments described with reference to FIG. 2B are specifically for use when a patient's heart is being paced. Referring to FIG. 2B, at a step 201, paced cardiac events are caused by pacing the patient's heart, using at least one electrode implanted within or on the patient's heart, with a voltage sufficient to cause capture. An exemplary pacemaker and leads that can be used to perform step 201 are described below with reference to FIGS. 3 and 4.

At step 204', an implanted sensor or implanted electrodes, remote from the patient's heart, is/are used to obtain a signal indicative of changes in arterial blood volume remote from the patient's heart while the patient's heart is being paced with the voltage sufficient to cause capture. Step 204' is similar to step 204 described above, except that at step 204' the obtained signal can be indicative of changes in arterial blood volume while the patient's heart is being paced, and at step 204 the obtained signal can be indicative of changes in arterial blood volume during intrinsic and/or paced beating of the patient's heart. Accordingly, step 204' need not be explained in further detail.

At step 208', one or more predetermined features of the signal indicative of changes in arterial blood volume obtained at step 204' is/are determined. At step 210', one or more metrics indicative of pulse arrival time (PAT) is/are determined by determining a time from a paced cardiac event caused at step 201 to one or more of the predetermined features of the signal indicative of changes in arterial blood volume detected at step 208'. At step 212', one or more estimate of the patient's arterial blood pressure is determined based on at least one of the one or more metrics indicative of PAT. Steps 208', 210' and 212' are similar to step 208, 210 and 212 discussed above, and thus additional details of these steps can be understood from the discussion above.

In accordance with certain embodiments, there is a determination of a value indicative of electromechanical delay (EMD) between delivery of pacing caused at step 201 and a mechanical cardiac contraction resulting from the pacing. In such embodiments, the metric(s) indicative of PAT determined at step 210' can also be determined based on the value indicative of EMD. For example, step 210' can be accomplished by determining a time from a paced cardiac event, caused at step 201, to a predetermined feature of the signal indicative of changes in arterial blood volume, detected at step 208', minus the determined value indicative of EMD. Additional details of how to determine a value indicative of a patient's EMD are discussed below with reference to FIG. 2C. It may be desirable to minimize the variance of EMD to improve a patient's HF condition. Accordingly, in certain embodiments, the pacing rate caused at step 201 can be adjusted to minimize variance of the value indicative of electromechanical delay (EMD).

In accordance with an embodiment, values indicative of SBP, DBP, PP and/or MAP, and potentially other information, are stored within memory of the implantable system for later analysis within the device and/or for later transmission to an external device. Such an external device (e.g., an external programmer or external monitor) can then be used to analyze such data.

Embodiments of the present invention are not limited to the exact order and/or boundaries of the steps shown in FIGS. 2A and 2B. In fact, many of the steps can be performed in a different order than shown, and many steps can be combined, or separated into multiple steps. For another example, certain steps shown in the FIGS. can be separated into two or more steps. The only time order is important is where a step acts on the results of a previous step.

In accordance with specific embodiments of the present invention, an alarm can be triggered based on comparisons of the values indicative of SBP, DBP, PP and/or MAP to corresponding thresholds, and/or based on comparisons of changes in values indicative of SBP, DBP, PP and/or MAP to corresponding thresholds. Such an alarm can be part of an implanted system. Alternatively, an implanted system can trigger a non-implanted alarm of a non-implanted system. In still other embodiments, where arterial pulse pressure information is transmitted (e.g., via telemetry) to an external device, a non-implanted alarm can be triggered.

In accordance with specific embodiments of the present invention, the method described with reference to FIG. 2A or 2B can be repeated from time-to-time, to thereby track changes in SBP, DBP, PP and/or MAP. For example, steps 202-212 can be performed periodically (e.g., once a minute, hour, day, week, or the like). The values indicative of SBP, DBP, PP and/or MAP can be compared in real time to corresponding thresholds. Alternatively, or additionally, values indicative of SBP, DBP, PP and/or MAP can be stored in memory of the implanted system. Such stored values can be analyzed by the implanted system and/or transmitted (e.g., via telemetry) to an external system (e.g., external programmer and external monitor) and analyzed by the external system. Use of various thresholds can be used to trigger alarms and/or therapy, as will be described below.

Depending on the frequency, periodic monitoring of arterial blood pressure may be costly in terms of energy, memory and/or processing resources. Accordingly, it may be more efficient to trigger the performance of certain steps upon detection of an event, such as a specific activity, or lack thereof, and/or a specific posture of the patient. For example, an activity sensor and/or posture sensor (e.g., sensor 415 in FIG. 4) can be used to trigger the performance of steps of FIG. 2A or 2B. For example, the steps of FIG. 2A or 2B can be triggered when it is detected that a patient is inactive and lying down. Additionally, or alternatively, such steps can be triggered when a patient is upright and walking. In still other embodiments, such steps can be triggered to occur, at specific intervals following a patient changing their posture (e.g., assuming an upright posture, or lying down) and/or activity level. For example, following a triggering event, values of arterial blood pressure can be determined once a minute for 10 minutes, or at 1 minute, 2 minutes, 5 minutes and 10 minutes after the triggering event. Of course, other variations are also possible, and within the scope of the present invention. It may also be that one or more specific step is performed substantially continually, but other steps are only performed in response to a triggering event or on demand.

It is normal for there to be a normal circadian variation in arterial blood pressure values, including SBP, DBP, PP and MAP values. For example, a drop in such values when a patient is sleeping, at rest and/or supine is normal. However, a drop in such values when a patient is active, or upright, or within a short period of a patient assuming an upright posture, is abnormal. Implanted activity and/or posture sensors (e.g., sensor 415 in FIG. 4) can thus be used to assist in defining when an alarm or the like should be triggered. For example, a posture sensor can be used to trigger the monitoring of arterial blood pressure values when a patient assumes an upright posture. In this manner, such monitoring can be used to determine whether a drop in blood pressure within a specific amount of time (e.g., 10 minutes), following the patient assuming of an upright position, exceeds a specified threshold. Such a threshold can be, e.g., an absolute value or a percentage. In specific embodiments, the SBP, DBP, PP and/or MAP thresholds to which determined SBP, DBP, PP and/or MAP values are compared can be based on the activity and/or posture of the patient.

Where at least some of steps of FIG. 2A or 2B are triggered in response to detection of various different activity and/or posture states, information about the patient's activity and/or posture can also be stored along with the arterial blood pressure information, so that such information can be correlated. In other words, there could be a cross-correlation of arterial blood pressure values with levels of activity and/or posture.

Accordingly, embodiments of the present invention can be used to determine, or assist with the determination of, whether there is a correlation between levels of arterial blood pressure, levels of activity and/or posture, and myocardial ischemic episodes experienced by a patient. Such information will enable a medical practitioner to analyze whether ischemic episodes that the patient experienced may have precipitated changes in arterial blood pressure, posture and/or activity.

In accordance with specific embodiments of the present invention, measures of arterial blood pressure, including values indicative of SBP, DBP, PP and/or MAP can be stored so that a physician or clinician can upload such measurements when visiting the physician or clinician.

More generally, measures of arterial blood pressure, obtained in accordance with embodiments of the present invention can be used to assess the hemodynamic status of a patient. This can include tracking a patient's cardiac disease state, including but not limited to, heart failure. For example, deviations from a baseline beyond a threshold in measures of arterial blood pressure over time can be interpreted as a worsening of a heart failure condition.

Figure 2C:
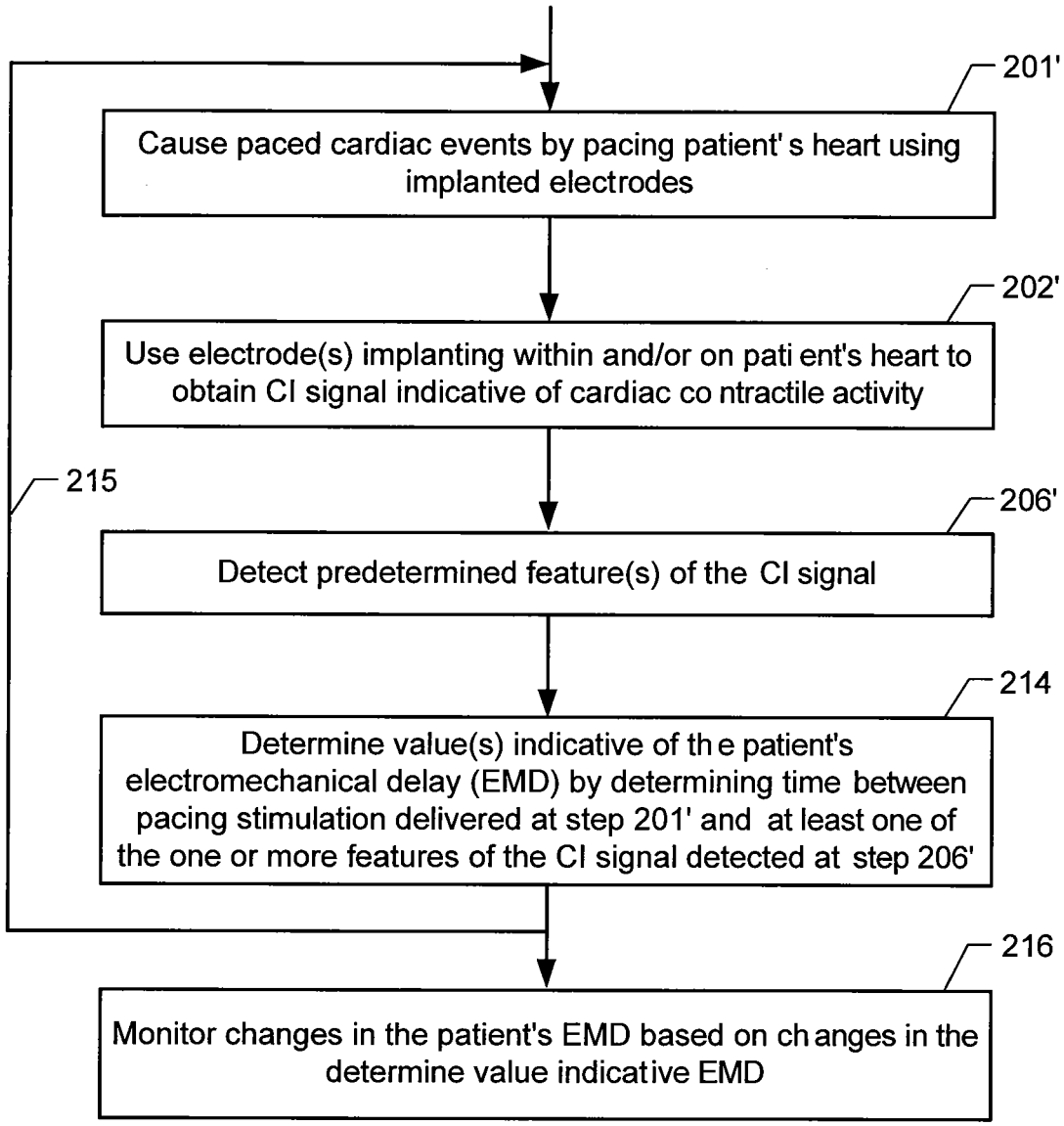
FIG. 2C is a high level flow diagram that is used to explain embodiments of the present invention that can be used to monitor an electro mechanical delay (EMD) of a patient's heart.

FIG. 2C will now be used to describe a method for monitoring a patient's electromechanical delay (EMD). At step 201' (which is similar to step 201 discussed with reference to FIG. 2B), paced cardiac events are cause by pacing the patient's heart, using implanted electrodes, with a voltage sufficient to cause capture. At step 202', implanted electrodes are used to obtain a cardiogenic impedance (CI) signal indicative of cardiac contractile activity while the patient's heart is being paced at step 201'. Step 202' is similar to step 202 described above with reference to FIG. 2A, except that the patient's heart is definitely being paced at step 202'. At step 206', in a similar manner as was discussed above with reference to step 206 in FIG. 2A, one or more predetermined features of the CI signal is detected.

Still referring to FIG. 2C, at step 214, one or more values indicative of the patient's EMD is/are determined by determining a time between pacing stimulation delivered at step 201' and one or more features of the CI signal detected at step 206'. As indicated by line 215, steps 201', 202', 206' and 214 are repeated from time to time (e.g., periodically, aperiodically, in response to a triggering event, etc.), with one or more values indicative of the patient's EMD determined each time. As indicated at step 216, changes in the patient's EMD can be monitored based on changes in at least one of the one or more values indicative EMD determined at step 214. For example, increases in a value indicative of EMD can be indicative of increases in EMD, and vise versa. This technique can be used, e.g., to monitor a patient's HF condition based on changes in the patient's EMD. For example, it is expected that a patient's EMD will increase as the patient's HF condition worsens, and will decrease if the patient's HF condition improves.

Additionally, or alternatively, the pacing can be adjusted in an attempt to reduce (and preferably minimize) variance of one or more values indicative of EMD, which is believed to improve an HF condition. Examples of pacing parameters that can be adjusted in an attempt to reduce the variance of one or more values indicative of EMD include, but are not limited to, pacing rate, atrio-ventricular delay, interventricular delay and interatrial delay.

EMD is believed to be affected by conduction abnormalities, myocardial contractility and cardiac diseases, including, but not limited to mitral stenosis, hypertension, and as mentioned above, HF. Accordingly, monitoring changes in EMD can also be useful for monitoring changes in conduction abnormalities, myocardial contractility and cardiac diseases.

As the term is being used herein, EMD is synonymous with pre-ejection period (PEP). Thus, a patient's PEP can be monitored using the embodiments of the present invention described above.

Exemplary Implantable System

Figure 3:
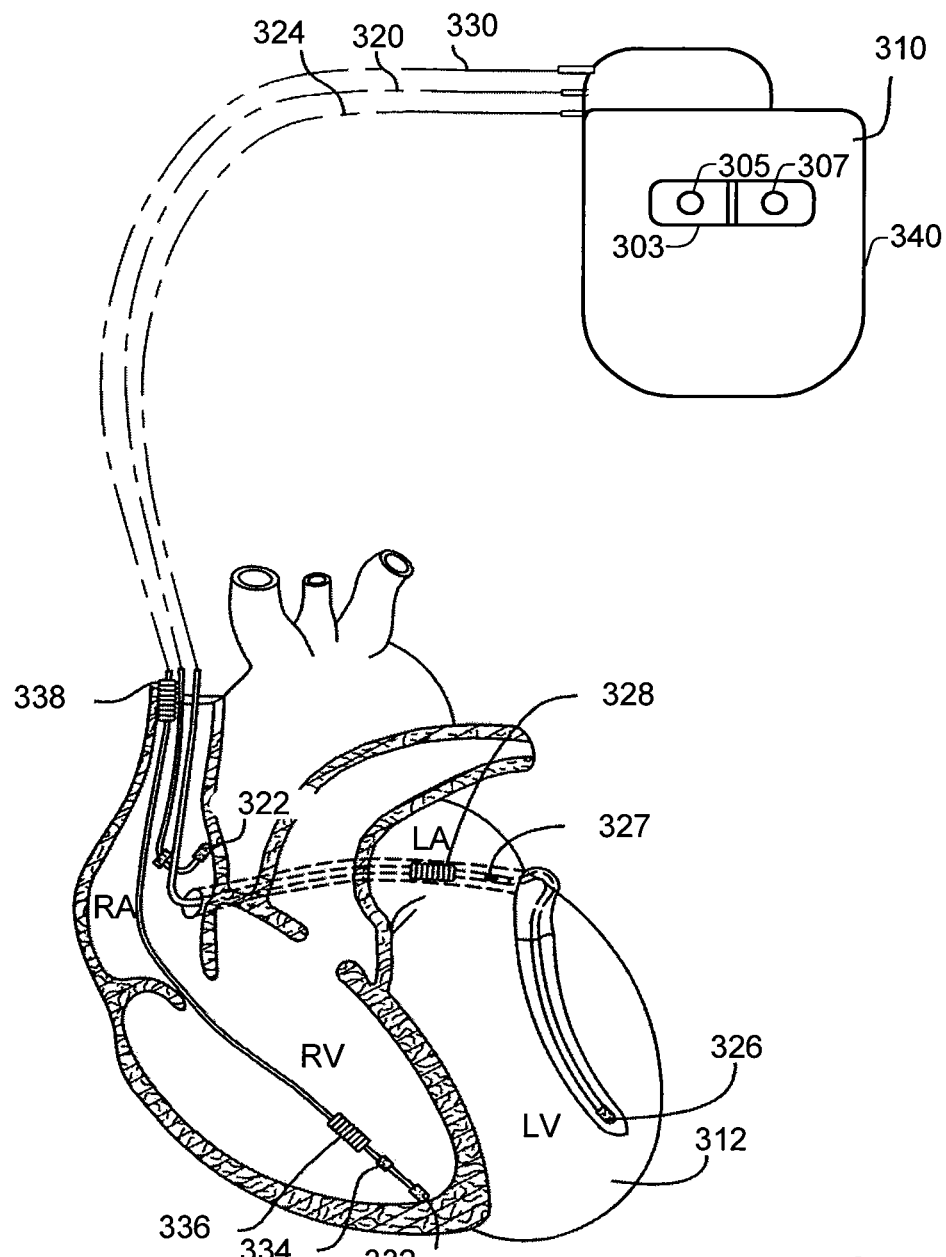
FIG. 3 illustrates an exemplary implantable cardiac stimulation device that includes a PPG sensor, and which can be used to perform various embodiments of the present invention.
Figure 4:
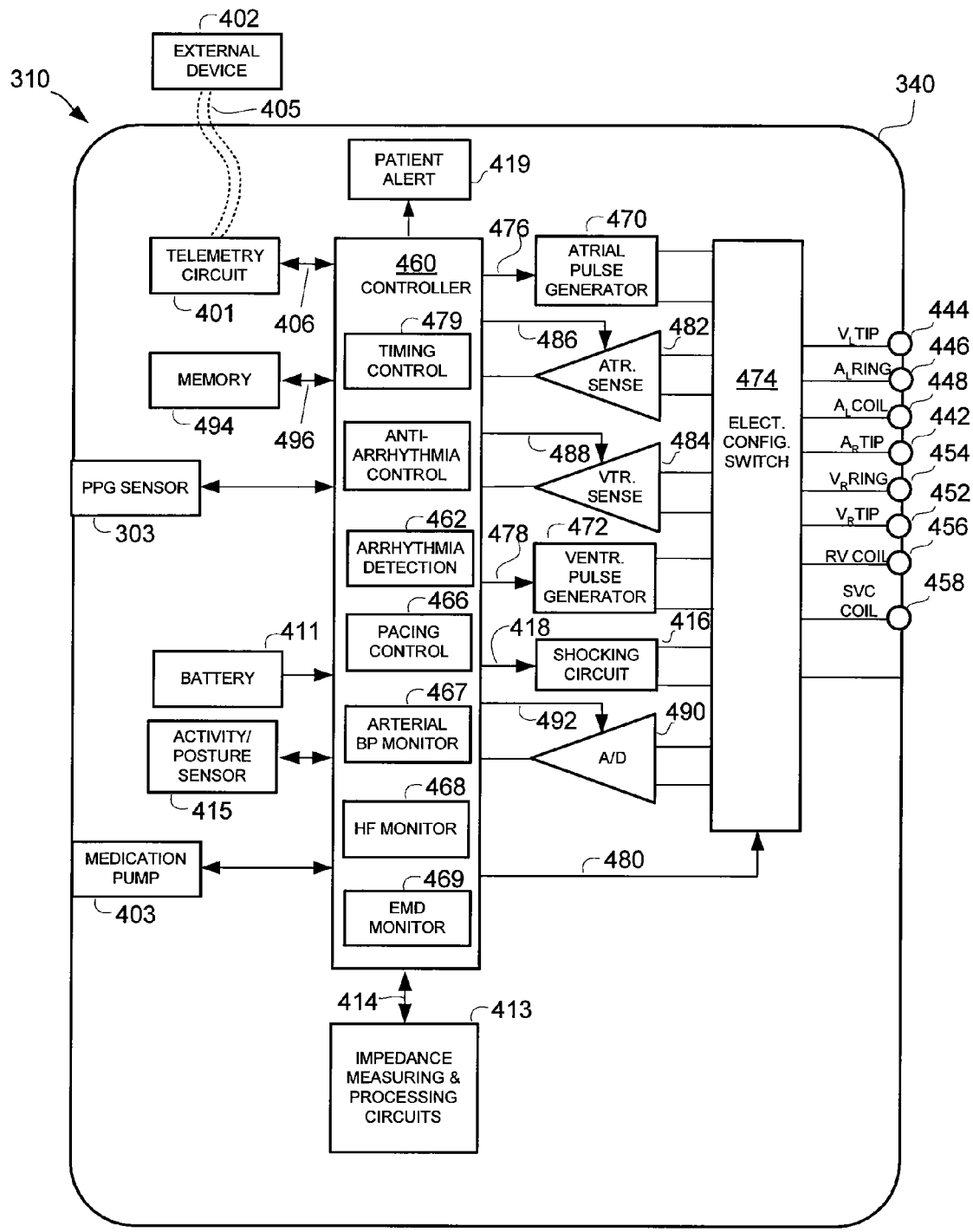
FIG. 4 is a simplified block diagram that illustrates possible components of the implantable device shown in FIG. 3.

FIGS. 3 and 4 will now be used to describe an exemplary implantable system that can be used to implement embodiments of the present invention including but not limited to monitoring a patient's arterial blood pressure, monitoring a patient's EMD and/or monitoring a patient's HF condition. Referring to FIG. 3, the implantable system is shown as including an implantable stimulation device 310, which can be a pacing device and/or an implantable cardioverter defibrillator. The device 310 is shown as being in electrical communication with a patient's heart 312 by way of three leads, 320, 324 and 330, which can be suitable for delivering multi-chamber stimulation and shock therapy. The leads can also be used to obtain CI, IEGM and/or IPG signals, for use in embodiments of the present invention. As described below, it is also possible that one of these leads (or another lead) can include an optical sensor (also referred to as a PPG sensor) that is useful for obtaining a PPG signal, similar to signal 122 shown in FIG. 1.

In FIG. 3, the implantable device 310 is shown as having a PPG sensor 303 (also referred to as an optical sensor) attached to its housing 340. The PPG sensor 303, which can be used to obtain a PPG signal similar to signal 122 shown in FIG. 1, includes a light source 305 and a light detector 307. The light source 305 can include, e.g., at least one light-emitting diode (LED), incandescent lamp or laser diode, but is not limited thereto. The light detector 307 can include, e.g., at least one photoresistor, photodiode, phototransistor, photodarlington or avalanche photodiode, but is not limited thereto. Light detectors are often also referred to as photodetectors or photocells.

The light source 305 outputs light that is reflected or backscattered by surrounding patient tissue, and reflected/backscattered light is received by the light detector 307. In this manner, changes in reflected light intensity are detected by the light detector, which outputs a signal indicative of the changes in detected light. The output of the light detector can be filtered and amplified. The signal can also be converted to a digital signal using an analog to digital converter, if the PPG signal is to be analyzed in the digital domain. A PPG sensor can use a single wavelength of light, or a broad spectrum of many wavelengths. Additional details of exemplary implantable PPG sensors are disclosed in U.S. Pat. Nos. 6,409,675 and 6,491,639, both entitled "Extravascular Hemodynamic Sensor" (both Turcott), which are incorporated herein by reference.

It is generally the output of the photodetector that is used to produce a PPG signal. However, there exist techniques where the output of the photodetector is maintained relatively constant by modulating the drive signal used to drive the light source, in which case the PPG signal is produced using the drive signal, as explained in U.S. Pat. No. 6,731,967, entitled "Methods and Devices for Vascular Plethysmography via Modulation of Source Intensity," (Turcott), which is incorporated herein by reference.

The PPG sensor 302 can be attached to a housing 340 of an implantable device, which as mentioned above can be, e.g., a pacemaker and/or an implantable cardioverter-defibrillator (ICD), or a simple monitoring device. Exemplary details of how to attach a sensor module to an implantable cardiac stimulation device are described in U.S. patent application Ser. No. 10/913,942, entitled "Autonomous Sensor Modules for Patient Monitoring" (Turcott et al.), filed Aug. 4, 2004, now U.S. Pat. No. 7,653,434, which is incorporated herein by reference. It is also possible that the PPG sensor 302 be integrally part of the implantable cardiac stimulation device 310. For example, the PPG sensor 302 can be located within the housing 340 of an ICD (and/or pacemaker) that has a window through which light can be transmitted and detected. In a specific embodiment, the PPG sensor 302 has a titanium frame with a light transparent quartz or sapphire window that can be welded into a corresponding slot cut in the housing of the ICD. This will insure that the ICD enclosure with the welded PPG sensor will maintain a hermetic condition.

Where the PPG sensor is incorporated into or attached to a chronically implantable device 310, the light source 305 and the light detector 307 can be mounted adjacent to one another on the housing or header of the implantable device, or on the bottom of the device, or at any other location. The light source 305 and the light detector 307 can be placed on the side of the implantable device 310 that, following implantation, faces the chest wall, and are configured such that light cannot pass directly from the source to the detector. The placement on the side of the device 310 that faces the chest wall maximizes the signal to noise ratio by directing the signal toward the highly vascularized musculature, and shielding the source and detector from ambient light that enters the body through the skin. Alternatively, at the risk of increasing susceptibility to ambient light, the light source 305 and the light detector 307 can be placed on the face of the device 310 that faces the skin of the patient. Other variations are also possible.

In an alternative embodiment, the PPG sensor 303 (or other plethysmography sensor) can be is remote from the housing 340 of the device 310, but communicates with the electronics in the device housing 340 via one or more wires, optical fibers, or wirelessly (e.g., using telemetry, RF signals and/or using body fluid as a communication bus medium). This embodiment enables an obtained PPG signal to be indicative of changes in arterial blood volume at a location remote from the patient's heart, where such location is also remote from the device housing 340. If desired, multiple PPG signals can be obtained, e.g., using multiple PPG sensors at different locations.

In another embodiment, optical fibers can be used to transmit light into and detect light from tissue that is remote from the device housing, even though the light source and light detector are located within or adjacent the device housing 140. This embodiment enables an obtained PPG signal to be indicative of changes in arterial blood volume at a location remote from the patient's heart, where such location is remote from the device housing 140, even though the light source 105 and light detector 107 are not remote from the housing. The distal end of the optical fiber(s) associated with the light source can be generally parallel to the distal end of the optical fiber(s) associated with the light detector, so that the light detector detects the portion of light reflected from tissue. Alternatively, the distal end of the optical fiber(s) associated with the light source can generally face the distal end of the optical fiber(s) associated with the light detector, with tissue therebetween, so that the light detector detects the portion of light transmitted through (as opposed to reflected from) the tissue therebetween.

In an embodiment, a PPG sensor can be within or attached to a lead that may extend from a main device housing 140. Accordingly, in this embodiment, a housing of the sensor module is sized to fit within the implantable lead. For example, the PPG can be located proximal from the distal tip of the lead so that the PPG sensor is sufficiently remote from the heart that variations in pulse transmission time are detectable and meaningful. The portion of the lead that is adjacent to a window of the PPG sensor module, where light is to exit and enter, should allow the light to pass in and out of the sensor. Thus, the lead may be transparent, or include its own window, opening, or the like. The lead can including tines for attaching the lead in its desired position, but may include any other type of fixation means (e.g., a pigtail shaped fixation means), or none at all. The lead can also have a suture sleeve, that enables the lead to be sutured to patient tissue. Additional details of a lead that includes an optical sensor that can be used to produce a PPG signal are provided in U.S. patent application Ser. No. 11/231,555, entitled "Improved Multi-Wavelength Implantable Oximeter Sensor" (Poore), filed Sep. 20, 2005 now U.S. Pat. No. 7,660,616, and U.S. patent application Ser. No. 11/282,198, entitled "Implantable Device with a Calibration Photodetector" (Poore), filed Nov. 17, 2005, now U.S. Pat. No. 7,840,246.

The implantable PPG sensor 303 obtains a PPG signal that after filtering is similar to signal 122 shown in FIG. 1, that pulsates over the cardiac cycle. Modulation of the signal occurs because arteries distend as the pressure wave created by the heart's pumping mechanism reaches the sensor site. Such a signal can be filtered and/or amplified as appropriate, e.g., to remove respiratory affects on the signal, and the like. Additionally, the signal can be digitized using an analog to digital converter. Exemplary techniques for performing filtering and other processing of a PPG signal (or other plethysmography signal) are explained with reference to FIGS. 6 and 7A-7E.

For much of above description, it has been assumed that the plethysmography sensor used to produce a plethysmography signal is a PPG sensor. Thus, the plethysmography signal has often been referred to as a PPG signal. However, it should be noted that other types of plethysmography sensors can alternatively be used. Thus, embodiments of the present invention should not be limited to use with PPG sensors and PPG signals. Further, as mentioned above, electrodes of the various leads can be used to obtain an IPG signal, and the IPG signal can be used in place of the PPG signal.

In specific embodiments, the plethysmography signal can be produced using non-radiant methods and devices, including, but not limited to mechanical strain, electrical impedance, or pressure. More specifically, rather than using a PPG sensor that includes a light source and detector, the implanted plethysmography sensor can include a strain gauge, a linear displacement sensor, or an ultrasound transducer, each of which is known in the art. Alternatively, an impedance plethysmography sensor, which is also known in the art, can be used. Details of exemplary implantable sensors that produce an impedance plethysmography signals are disclosed, e.g., in U.S. Pat. Nos. 4,674,518, 4,686,987 and 5,334,222 (all to Salo), which are incorporated herein by reference.

Still referring to FIG. 3, to sense atrial cardiac signals and to provide right atrial chamber stimulation therapy, the device 310 is coupled to an implantable right atrial lead 320 having at least an atrial tip electrode 322, which typically is implanted in the patient's right atrial appendage. To sense left atrial and ventricular cardiac signals and to provide left-chamber pacing therapy, the device 310 is coupled to a "coronary sinus" lead 324 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328.

The device 310 is also shown in electrical communication with the patient's heart 312 by way of an implantable right ventricular lead 330 having, in this embodiment, a right ventricular tip electrode 332, a right ventricular ring electrode 334, a right ventricular (RV) coil electrode 336, and an SVC coil electrode 338. Typically, the right ventricular lead 330 is transvenously inserted into the heart 312 so as to place the right ventricular tip electrode 332 in the right ventricular apex so that the RV coil electrode 336 will be positioned in the right ventricle and the SVC coil electrode 338 will be positioned in the superior vena cava. Accordingly, the right ventricular lead 330 is capable of receiving cardiac signals and delivering stimulation in the form of pacing and shock therapy to the right ventricle.

FIG. 4 will now be used to provide some exemplary details of the components of the implantable devices 310. Referring now to FIG. 4, the implantable devices 310, and alternative versions thereof, can include a microcontroller 460. As is well known in the art, the microcontroller 460 typically includes a microprocessor, or equivalent control circuitry, and can further include RAM and/or ROM memory, logic and timing circuitry, state machine circuitry and/or I/O circuitry. Typically, the microcontroller 460 includes the ability to process or monitor input signals (data) as controlled by a program code stored in a designated block of memory. The details of the design of the microcontroller 460 are not critical to the present invention. Rather, any suitable microcontroller 460 can be used to carry out the functions described herein. The use of microprocessor-based control circuits for performing timing and data analysis functions are well known in the art. In specific embodiments of the present invention, the microcontroller 460 performs some or all of the steps associated with determining estimates of SBP, DBP, PP, MAP, EMD and/or HF. Additionally, the microcontroller 460 may detect arrhythmias, and select and control delivery of anti-arrhythmia therapy.

Representative types of control circuitry that may be used with embodiments of the present invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

Depending on implementation, the device 310 can be capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation. For example, if the implantable device is a monitor that does not provide any therapy, it is clear that many of the blocks shown may be eliminated.

The housing 340, shown schematically in FIG. 4, is often referred to as the "can", "case" or "case electrode" and may be programmably selected to act as the return electrode for all "unipolar" modes. The housing 340 may further be used as a return electrode alone or in combination with one or more of the coil electrodes, 128, 136 and 138, for shocking purposes. The housing 340 can further include a connector (not shown) having a plurality of terminals, 442, 444, 446, 448, 452, 454, 456, and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 322.

To achieve left atrial and ventricular sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular tip electrode 326, the left atrial ring electrode 327, and the left atrial coil electrode 328, respectively.

To support right ventricle sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 332, right ventricular ring electrode 334, the RV coil electrode 336, and the SVC coil electrode 338, respectively.

An atrial pulse generator 470 and a ventricular pulse generator 472 generate pacing stimulation pulses for delivery by the right atrial lead 320, the right ventricular lead 330, and/or the coronary sinus lead 324 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators, or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, etc.) by selectively closing the appropriate combination of switches (not shown) as is known in the art.

Atrial sensing circuits 482 and ventricular sensing circuits 484 may also be selectively coupled to the right atrial lead 320, coronary sinus lead 324, and the right ventricular lead 330, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers, or shared amplifiers. The switch 474 determines the "sensing polarity" of the cardiac signal by selectively closing the appropriate switches, as is also known in the art. In this way, the clinician may program the sensing polarity independent of the stimulation polarity.

Each sensing circuit, 482 and 484, preferably employs one or more low power, precision amplifiers with programmable gain and/or automatic gain control, band-pass filtering, and a threshold detection circuit, as known in the art, to selectively sense the cardiac signal of interest. The automatic gain control enables the device 310 to deal effectively with the difficult problem of sensing the low amplitude signal characteristics of atrial or ventricular fibrillation. Such sensing circuits, 482 and 484, can be used to determine cardiac performance values used in the present invention. Alternatively, an automatic sensitivity control circuit may be used to effectively deal with signals of varying amplitude.

The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity, in the appropriate chambers of the heart. The sensing circuits, 482 and 484, in turn, receive control signals over signal lines, 486 and 488, from the microcontroller 460 for purposes of measuring cardiac performance at appropriate times, and for controlling the gain, threshold, polarization charge removal circuitry (not shown), and timing of any blocking circuitry (not shown) coupled to the inputs of the sensing circuits, 482 and 486.

For arrhythmia detection, the device 310 includes an arrhythmia detector 462 that utilizes the atrial and ventricular sensing circuits, 482 and 484, to sense cardiac signals to determine whether a rhythm is physiologic or pathologic. The timing intervals between sensed events (e.g., P-waves, R-waves, and depolarization signals associated with fibrillation) can be classified by the microcontroller 460 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). Additionally, the arrhythmia detector 462 can perform arrhythmia discrimination, e.g., using measures of arterial blood pressure determined in accordance with embodiments of the present invention. The arrhythmia detector 462 can be implemented within the microcontroller 460, as shown in FIG. 4. Thus, this detector 462 can be implemented by software, firmware, or combinations thereof. It is also possible that all, or portions, of the arrhythmia detector 462 can be implemented using hardware. Further, it is also possible that all, or portions, of the ischemia detector 462 can be implemented separate from the microcontroller 460.

In accordance with an embodiment of the present invention, the implantable device 310 includes an arterial blood pressure monitor 467, a heart failure monitor 468 and an electromechanical delay monitor 469, which can be used to estimate SBP, DBP, PP, MAP, EMD and/or HF (and/or changes therein), using the techniques described above. The monitors 467, 468 and 469 can be implemented within the microcontroller 460, as shown in FIG. 4, and can the be implemented by software, firmware, or combinations thereof. It is also possible that all, or portions, of the monitors 467, 468 and/or 469 to be implemented using hardware. Further, it is also possible that all, or portions, of the monitors 467, 468 and/or 469 can be implemented separate from the microcontroller 460. The monitors 467, 468 and/or 469 can be used in a closed loop control system to provide an assessment of hemodynamic condition during pacing parameter adjustments, and/or as an assessment of hemodynamic condition during a detected arrhythmia. Such measures of hemodynamic condition can be used when determining which anti-arrhythmia therapy options are appropriate. It is also noted that monitors 467, 468 and/or 469 can be combined into a single monitor, or separated into further blocks.

The implantable device 310 can also include a pacing controller 466, which can adjust a pacing rate and/or pacing intervals based on estimates of SBP, DBP, PP, MAP, EMD and/or HF, in accordance with embodiments of the present invention. The pacing controller 466 can be implemented within the microcontroller 460, as shown in FIG. 4. Thus, the pacing controller 466 can be implemented by software, firmware, or combinations thereof. It is also possible that all, or portions, of the pacing controller 466 can be implemented using hardware. Further, it is also possible that all, or portions, of the pacing controller 466 can be implemented separate from the microcontroller 460.

The implantable device can also include a medication pump 403, which can deliver medication to a patient if the patient's SBP, DBP, PP, MAP, EMD and/or HF fall outside certain thresholds or ranges. Information regarding implantable medication pumps may be found in U.S. Pat. No. 4,731,051 (Fischell) and in U.S. Pat. No. 4,947,845 (Davis), both of which are incorporated by reference herein.

Still referring to FIG. 4, cardiac signals are also applied to the inputs of an analog-to-digital (A/D) data acquisition system 490. The data acquisition system 490 can be configured to acquire various signal, including but not limited to, CI, IEGM, PPG and IPG signals, convert the raw analog data into a digital signal, and store the digital signals for later processing and/or telemetric transmission to an external device 402. The data acquisition system 490 can be coupled to the right atrial lead 320, the coronary sinus lead 324, and the right ventricular lead 330 through the switch 474 to sample cardiac signals across any pair of desired electrodes.

The data acquisition system 490 can be coupled to the microcontroller 460, or other detection circuitry, for detecting an evoked response from the heart 312 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 460 detects a depolarization signal during a window following a stimulation pulse, the presence of which indicates that capture has occurred. The microcontroller 460 enables capture detection by triggering the ventricular pulse generator 472 to generate a stimulation pulse, starting a capture detection window using the timing control circuitry 479 within the microcontroller 460, and enabling the data acquisition system 490 via control signal 492 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 460 is further coupled to the memory 494 by a suitable data/address bus 496, wherein the programmable operating parameters used by the microcontroller 460 are stored and modified, as required, in order to customize the operation of the implantable device 310 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 312 within each respective tier of therapy. The memory 494 can also store data including information about estimates of SBP, DBP, PP, MAP, EMD and/or HF.

The operating parameters of the implantable device 310 may be non-invasively programmed into the memory 494 through a telemetry circuit 401 in telemetric communication with an external device 402, such as a programmer, transtelephonic transceiver, or a diagnostic system analyzer. The telemetry circuit 401 can be activated by the microcontroller 460 by a control signal 406. The telemetry circuit 401 advantageously allows intracardiac electrograms and status information relating to the operation of the device 310 (as contained in the microcontroller 460 or memory 494) to be sent to the external device 402 through an established communication link 404. The telemetry circuit can also be use to transmit arterial blood pressure data to the external device 402.

For examples of telemetry devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 310 additionally includes a battery 411 which provides operating power to all of the circuits shown in FIG. 4. If the implantable device 310 also employs shocking therapy, the battery 411 should be capable of operating at low current drains for long periods of time, and then be capable of providing high-current pulses (for capacitor charging) when the patient requires a shock pulse. The battery 411 should also have a predictable discharge characteristic so that elective replacement time can be detected.

The implantable device 310 is also shown as including an activity and/or posture sensor 415. Such a sensor 415 can be a simple one dimensional sensor that converts mechanical motion into a detectable electrical signal, such as a back electro magnetic field (BEMF) current or voltage, without requiring any external excitation. Alternatively, the sensor 415 can measure multi-dimensional activity information, such as two or more of acceleration, direction, posture and/or tilt. Examples of multi-dimensional activity sensors include, but are not limited to: the three dimensional accelerometer-based position sensor disclosed in U.S. Pat. No. 6,658,292 to Kroll et al., which is incorporated herein by reference; the AC/DC multi-axis accelerometer disclosed in U.S. Pat. No. 6,466,821 to Pianca et al., which in incorporated herein by reference; and the commercially available precision dual-axis accelerometer model ADXL203 and three-axis accelerometer model ADXL346, both available from Analog Devices of Norwood, Mass.

The implantable device 310 can also include a magnet detection circuitry (not shown), coupled to the microcontroller 460. It is the purpose of the magnet detection circuitry to detect when a magnet is placed over the implantable device 310, which magnet may be used by a clinician to perform various test functions of the implantable device 310 and/or to signal the microcontroller 460 that the external programmer 402 is in place to receive or transmit data to the microcontroller 460 through the telemetry circuits 401.

As further shown in FIG. 4, the device 310 is also shown as having an impedance measuring and processing circuit 413 which is enabled by the microcontroller 460 via a control signal 414 and can be used for obtaining many types of bodily and intracardiac impedances, including a network of single- or multi-vector impedance measurements. Such impedance measurements can be used, e.g., for trending many kinds of physiological variables, and can also be used for detection of air movement in and out of the lungs, blockage of airways, lead impedance surveillance during acute and chronic phases for proper lead positioning or dislodgement; lead integrity by detecting insulation abrasion, operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 413 may be coupled to the switch 474 so that any desired electrodes may be used, and networks of vectors can be selected. The impedance measuring circuit 413 can be used to obtain cardiogenic impedance (CI) signals, which can be used with certain embodiments of the present invention. Exemplary details of an impedance measuring and processing circuit 413 are provided in, and discussed with reference to FIG. 5. Additional exemplary details of circuitry for obtaining CI signals are provided in U.S. patent application Ser. No. 11/863,516, filed Sep. 28, 2007 and entitled "Use of Cardiogenic Impedance Waveform Morphology to Analyze Cardiac Conditions and to adjust Treatment Therapy," which is incorporated herein by reference. The impedance measuring circuit 413, when measuring impedance using implanted electrodes that are remote from the patient's heart, can be used to obtain impedance plethysmography (IPG) signals, which can be used in certain embodiments of the present invention.

In the case where the implantable device 310 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 460 further controls a shocking circuit 416 by way of a control signal 418. The shocking circuit 416 generates shocking pulses of low (up to 0.5 Joules), moderate (0.5-10 Joules), or high energy (11 to 40 Joules), as controlled by the microcontroller 460. Such shocking pulses are applied to the patient's heart 312 through at least two shocking electrodes, and as shown in this embodiment, selected from the left atrial coil electrode 328, the RV coil electrode 336, and/or the SVC coil electrode 338. As noted above, the housing 340 may act as an active electrode in combination with the RV electrode 336, or as part of a split electrical vector using the SVC coil electrode 338 or the left atrial coil electrode 328 (i.e., using the RV electrode as a common electrode).

The above described implantable device 310 was described as an exemplary pacing device. One or ordinary skill in the art would understand that embodiments of the present invention can be used with alternative types of implantable devices. Accordingly, embodiments of the present invention should not be limited to use only with the above described device.

Exemplary CI Circuit

Figure 5:
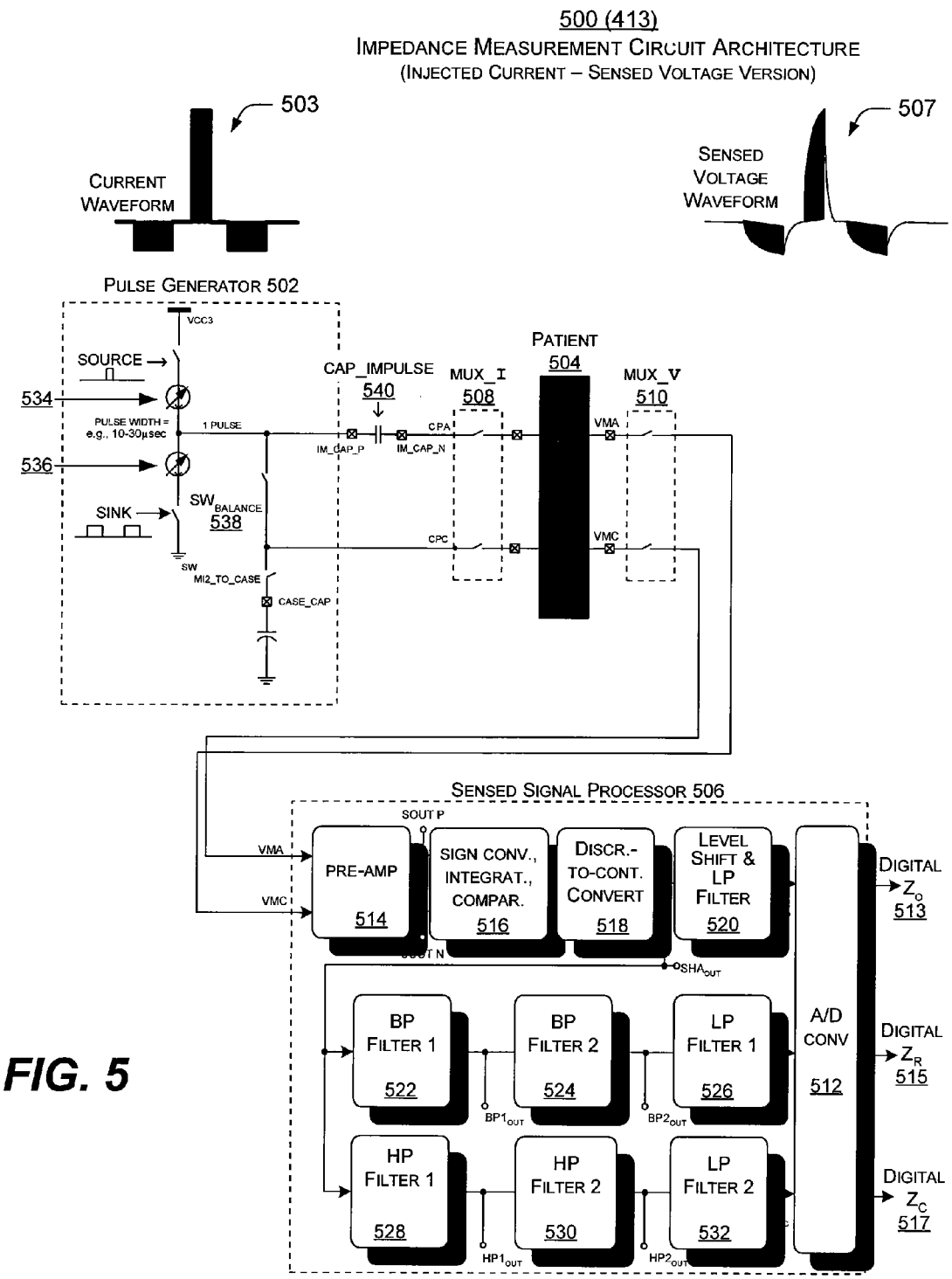
FIG. 5 is a block diagram of an exemplary impedance measuring circuit architecture that can be used to obtain CI signals and/or IPG signals that can be used in various embodiments of the present invention.

For completeness, FIG. 5 shows an exemplary impedance measurement circuit architecture 500 (e.g., which can be used to implement block 278 on FIG. 2), including filter components to obtain raw, cardiogenic, and respiratory impedances. The illustrated architecture 500 is just one example configuration, other configurations are also possible. In one implementation, the exemplary impedance measurement architecture 500 includes a pulse generator 502 for generating an exemplary pulse waveform, in this case a current waveform 503, for application to the bodily tissue of a patient 504 and a sensed signal processor 506 for processing resulting waveforms detected in the tissue, in this case voltage waveforms 507. The pulse generator 502 can be implemented by the circuitry of blocks 470 or 472 in FIG. 4, or dedicated circuitry. An injection (e.g., current pulse) multiplexor 508 implements the single- or multi-vector aspect of signal application by determining a first set of electrodes for injecting the exemplary waveform 503. The selection of electrodes may be determined, e.g., by the controller 460 (FIG. 4), or a dedicated vector engine (not shown). Likewise, a sensing (voltage measurement) multiplexer 510 implements signal sensing by determining a second set of electrodes for sensing the resulting voltage waveforms 507. The set of sensing electrodes may also be determined, e.g., by the controller 460 (Fig. 4), or a dedicated vector engine (not shown). Both the injection multiplexor 508 and the sensing multiplexor 510 may be implemented in the implantable device 310 in the electrode configuration switch 474 (Fig. 4).

A waveform 503 for application to bodily tissue that is generated by the exemplary impedance measurement circuit architecture 500 can possess special waveform features and electrical characteristics that are well suited for probing and measuring many types of physiological parameters in the body using current modulated or voltage modulated pulses. Examples of such waveforms are described in U.S. patent application Ser. No. 11/684,664, entitled "Tissue Characterization Using Intracardiac Impedances with an Implantable Lead System", (Wong et al), filed Mar. 12, 2007, which are incorporated herein by reference. Exemplary waveforms 503 are multi-phasic, with negative phases (pulse segments below baseline) that balance positive phases (pulse segments above baseline). The illustrated waveform 503 is tri-phasic. Other versions of the waveform 503 may have more than three phases, may be synchronous or asynchronous, may be rectangular or sinusoidal, etc. In one variation, the exemplary impedance measurement architecture applies the waveform 503 as a voltage waveform instead of a current waveform and senses the results as electrical current instead of voltage.

Properties of the exemplary waveforms 503 include superior penetration of some tissues than conventionally injected signals; better differential penetration of tissues than conventionally injected signals for improved differentiation and characterization of tissues; broader frequency spectrum content than conventionally injected signals in order to characterize tissue; greater neutrality in the body than conventionally injected signals, i.e., the exemplary waveforms do not change the parameter they are trying to measure, and moreover, do not create ionic imbalances or imbalances of charge, voltage, etc., in the tissues or at tissue-electrode interfaces.

Each waveform 503 preferably has a total duration less than the charging time constant of the electrode-electrolyte interfaces used to inject and sense the signals. These time constants are typically in the range of a few milliseconds. In one implementation, the duration of waveform 503 is less than 1 millisecond. This waveform feature is helpful for minimizing polarization effects at these electrode-electrolyte interfaces. Other features of the exemplary waveforms 503 include symmetric or asymmetric phase duration, decreasing phase amplitudes, and alternating phase signs. Each waveform 503 typically has null durations in between phases to provide time to allow complete processing of information caused by one phase before the next phase of the waveform 503 begins. Implementations of the waveform 503 that have near perfect square wave pulses (or rectangular wave pulses) contain a great deal of high-frequency content. Near-sinusoidal implementations of the waveform 503 may contain less high frequency content than the rectangular wave versions.

The features of exemplary waveforms 503 just enumerated provide numerous advantages, including: eliminating the need for fast digital sampling, minimizing artifacts introduced in the measurement process, increased tolerance of small phase delays between injected and sensed signals. The exemplary waveforms 503 also lend themselves to CMOS realization using low-value switched capacitor solutions. Further, the wide frequency spectrum of the injected signal can be used to implement algorithms that differentiate tissues based on their frequency response, and/or phase delay. The very low duty-cycle of the exemplary waveforms 503 make them safer for patients. The reduced duty-cycle brings the injected charge and the root-mean-square value of the injected signal well below levels that could be perceived by the patient or that could induce adverse events.

It is noted that the net-zero voltage feature, also referred to as the voltage-balanced feature, refers to the voltage formed on blocking capacitors that appear in series with the load. The flow of current through these capacitors builds up voltage across them. Since these capacitors, such as capacitor 540 in FIG. 5, also appear in circuits that are responsible for sensing cardiac activity, it is important that the net voltage built up on them be zero. As a result of the net-zero voltage feature, the influence of an exemplary waveform 503 on the circuits that sense cardiac activity is minimal.

Other features of the exemplary waveforms 503 derive from the above-mentioned null segments—intra-waveform segments containing no signal—that serve several purposes. First, the null segments allow the electronics in processing circuits to settle during measurement of phases and second, they allow multiple instances of the waveform 503 to exist in the patient's tissue simultaneously, being staggered by time multiplexing such that a phase of one waveform can be measured during the time that there is no signal between phases of another waveform.

In one implementation, the exemplary waveform 503 is used to derive physiological measurements based on intracardiac impedances. Based on such cardiogenic impedance measurements, many physiological variables can be trended to detect changes in a patient's condition, such as congestive heart failure (CHF) index, pulmonary edema, systolic slope, contraction (e.g., dZ/dt(max)), diastolic slope, relaxation (e.g., dZ/dt(min)), pre-ejection period (in low resolution), ejection time, left ventricular ejection fraction (LVEF), diastolic heart failure index (DHFI), cardiac index, etc.

The exemplary waveform 503 provides an elegant and reliable vehicle for measuring bodily impedances in a manner that gives reliably reproducible results. Instead of a conventional technique of trying to sense an instantaneous "snapshot" measurement of a conventionally injected signal, the impedance measurement circuit architecture 500 derives an impedance measurement by dividing the area under the sensed voltage curve (waveform 507) by the area of the injected current waveform 503. An exemplary implantable device 310 can perform this exemplary method by "integrating the curve" of an absolute value of waveforms 503 or 507. Sometimes the exemplary implantable device can closely approximate this integration without having to perform an integration operation by directly measuring and summing the area "under" the curve (e.g., under the rectangular wave) of the waveform 503, that is, the area composed of the absolute value of the three areas of the three phases of an exemplary tri-phasic waveform 503.

Likewise, the exemplary implantable device can integrate, or closely approximate the integration, by measuring and summing the area "under" the curve (e.g., the rectangular wave) of the waveform 507, that is, the area composed of the absolute value of the three areas of the three phases. In one implementation, the area of the sensed voltage, waveform 507, is measured at the output of an integrator circuit. The area of the injected current, waveform 503, is computed by, or preset by, the micro-controller driving the implantable device. An implantable device 310 may thus use this area-based ("areal") approach to deriving a network of impedance measurements over a multi-vector network 350.

Returning to description of the impedance measurement circuit architecture 500 itself, the sensed signal processor 506 typically consists of pre-amplification circuitry, switched capacitor filters, and an analog to digital converter 512. In one implementation, the voltage signal from the voltage measurement multiplexer 510 is processed by several voltage measurement lines or paths. The illustrated sensed signal processor 506 is able to obtain at least the three different impedance signals introduced above with respect to FIG. 5, that is, low frequency raw impedance $Z_o$ 513, respiration impedance $Z_r$ 515, and cardiogenic impedance $Z_c$ 517. Each measurement can be activated separately or simultaneously.

A digital form of raw impedance $Z_o$ 513 may be obtained. First, the sensed signal, i.e., the tri-phasic voltage waveform 507 from the voltage measurement multiplexer 510, is sent to a preamplifier 514. The next stage is embodied in a sign conversion and integration module 516. At this stage, the signal is converted into an absolute value and then integrated over time. Using the integration process instead of conventional instantaneous "snapshot" measurements of impedance components such as pure resistance produces results that are more noise-free and more accurate than the conventional techniques.

The signal is then applied to a discrete-to-continuous signal conversion module 518. At this point in the architecture 500, the signals for low frequency impedance $Z_o$ 513, respiration impedance $Z_r$ 515, and cardiogenic impedance $Z_c$ 517 (also referred to as the CI signal) are extracted separately by different filter paths, as summarized in FIG. 5. To obtain the low frequency impedance $Z_o$ 513, the signal is sent to a level shift and low pass filter module 520, and then to the analog to digital converter 512.

A digital form of the respiration impedance $Z_r$ 515 may be obtained by tapping the analog signal from the input of the level shift and low pass filter module 520, and feeding the signal to a line consisting of band-pass filters 522 and 524 and a low pass filter 526. The signal is then fed to the analog to digital converter 512 to obtain digital $Z_r$ 515.

A digital form of the cardiogenic impedance $Z_c$ 517 (also referred to as the CI signal) may likewise be obtained by tapping the analog signal from the input of the level shift and low pass filter module 520, and feeding the signal to a line consisting of high pass filters 528 and 530 and a low pass filter 532. The signal is then fed to the analog to digital converter 512 to obtain digital $Z_c$ 517.

In one implementation, the pulse generator 502 consists of two timing controlled current generators 534 and 536 with programmable magnitude. The first current generator 534 sources current, the other current generator 536 sinks the current. As part of the charge and voltage balancing process, the switch $SW_{Balance}$ 538 is used to discharge the external capacitor Cap_Impulse 540 after each generated impulse. The pulse rate is programmable.

Components of the impedance measurement architecture 500 may be implemented in the impedance measuring and processing circuit 413 shown in FIG. 4, and may be implemented in hardware, software, or combinations thereof. For example, the exemplary impedance measurement architecture 500 may be implemented in hardware as part of the microcontroller 460 and/or as hardware integrated into the fabric of the exemplary implantable device 310; or as software/firmware instructions programmed into an implementation of the implantable device 310 and executed on the microcontroller 421 during certain modes of operation.

In one implementation, the preamplifier 514 is included in the impedance measuring & processing circuits 478. The pulse generator 502 can be implemented in the impedance processing module 440 as may some of the other components of the sensed signal processor 506.

Although the illustrated version of the impedance measurement circuit architecture 500 applies a current pulse waveform 503 and senses a voltage pulse waveform 507, other implementations can inject a voltage waveform and sense a current waveform.

The "raw" impedance measurement, $Z_o$ 513, can be useful for determining extra- or intra-cardiac impedances and examining conditions such as pulmonary edema. The cardiogenic component of impedance, $Z_c$ 517, can be used in the various embodiments of the invention described in detail above.

Processing of Plethysmography Signals

Photoplethysmography (PPG) and Impedance Plethysmography signals (collectively referred to as PPG/IPG signals), and other plethysmography signals, show changes in a patient's arterial system as a result of the patient's heart contracting, and such signals are indicative of changes in arterial blood volume. A PPG signal can be obtained using a PPG sensor, which as explained above, can be an optical sensor including a light source and a light detector. An IPG signal can be obtained using an IPG sensor, which as explained above, can include electrodes and circuitry used to measure the impedance between such electrodes. One or more such electrodes can be located on one or more leads, and/or a mechanical housing of an implanted device can act as one of the electrodes.

When a PPG/IPG sensor is implanted at a location remote from the patient's heart, an obtained pressure pulsation signal has been shown to arrive from the heart to the PPG/IPG sensor after an amount of time that is related to arterial blood pressure. The velocity of the pressure pulsation traversing the arteries is positively correlated with systolic blood pressure. Therefore, as explained above, measures of pulse arrival time (PAT), and metrics indicative of PAT, can be used to estimate arterial blood pressure.

Better estimates of arterial blood pressure can be obtained if the PPG/IPG signals used in the above described embodiments are appropriately processed. Accordingly, certain embodiments of the present invention relate to techniques for processing PPG/IPG signals (or other plethysmography signals), as described below. Further embodiments of the present invention, described below, relate to how to extract features of PPG/IPG signals (or other plethysmography signals), which features can be used to determine metrics indicative of PAT, in the manners explained above.

Figure 6:
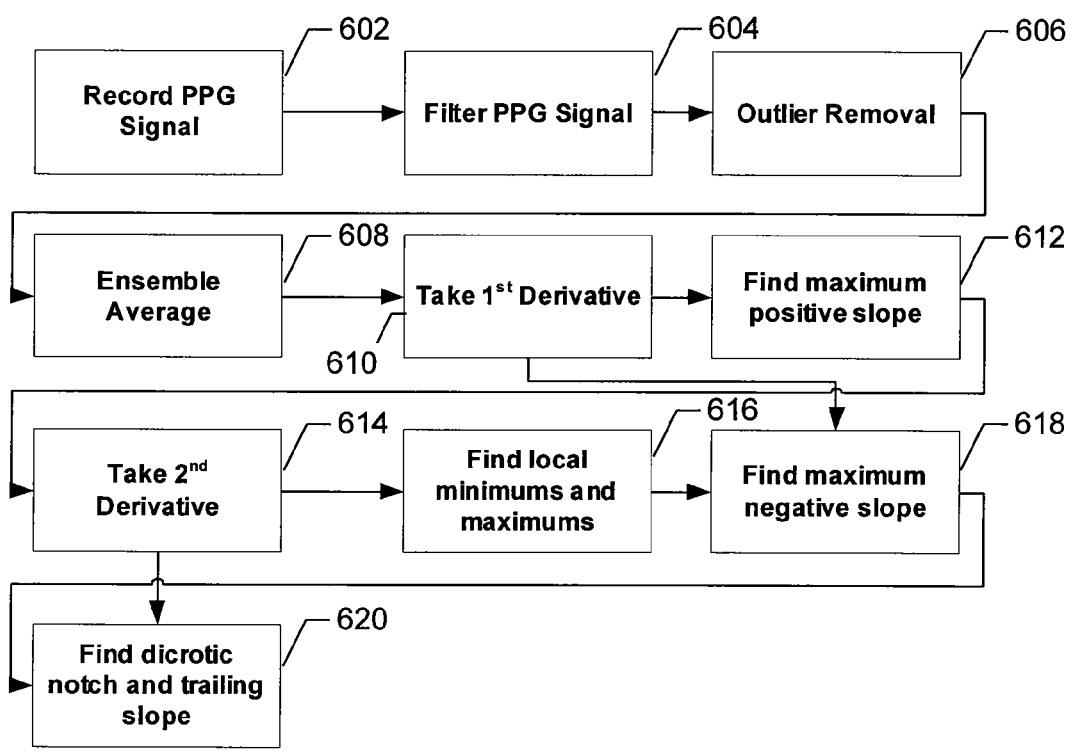
FIG. 6 is a flow diagram that is used to describe how features of a PPG or IPG signal can be detected in accordance with specific embodiments of the present invention.
Figure 7A:
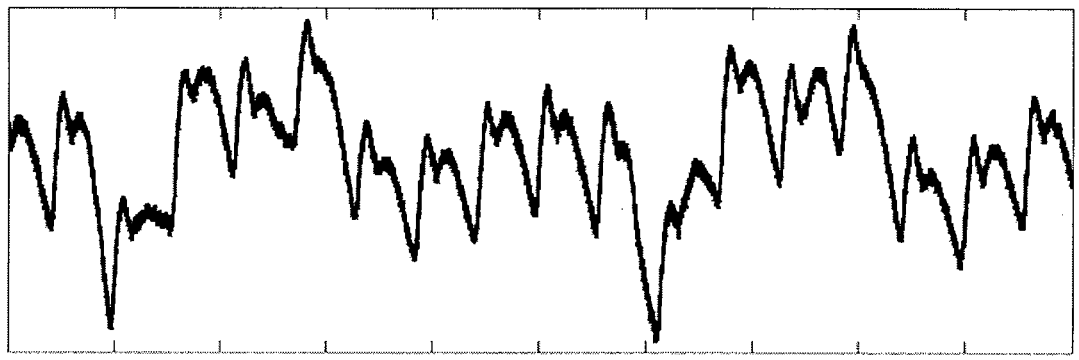
FIG. 7A illustrates an exemplary raw PPG signal over 20 seconds.

FIGS. 6 and 7A-7E will now be used to describe exemplary embodiments for obtaining a PPG signal and detecting predetermined features of the PPG signal. Similar techniques can be used to obtain an IPG signal (or other plethysmography signal) and detect predetermined features of the IPG signal (or other plethysmography signal). Referring to FIG. 6, at step 602 a PPG signal is recorded. Recording of a PPG signal may be triggered, e.g., on an R wave, based on respiratory cycle, based on activity levels, etc. An exemplary raw PPG signal recorded over 20 second is shown in FIG. 7A.

Figure 7B:
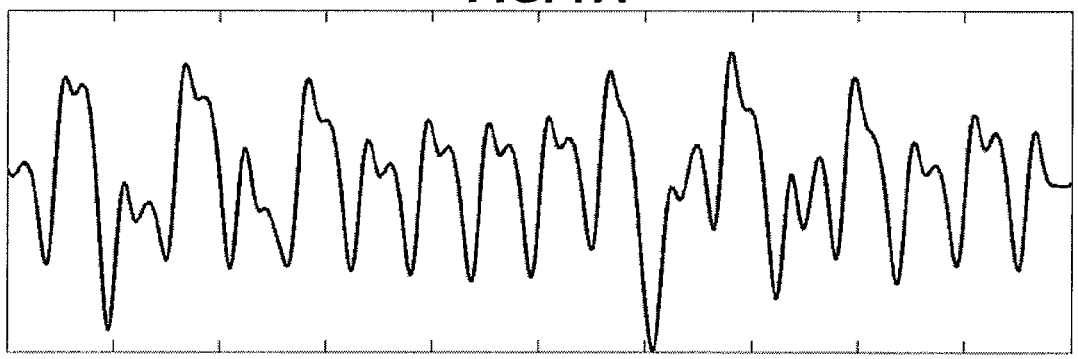
FIG. 7B illustrates the PPG signal of FIG. 7A after it has been band-passed filtered, which caused a reduction in noise due to respiration, high frequency noise, and motion artifacts.

At step 604, the PPG signal is filtered to remove respiratory noise, motion artifact, baseline drift, etc. For example, the signal can be band-pass filtered so that the pass-band is from about 0.7 to 10 Hz, although other pass bands can be used. FIG. 7B shows the raw PPG signal of FIG. 7A, after being band-passed filtered using a pass-band of about 0.7 to 10 Hz. As can be appreciated from FIG. 7B, most of the respiration signal and high frequency noise is removed by the filtering.

Figure 7C:
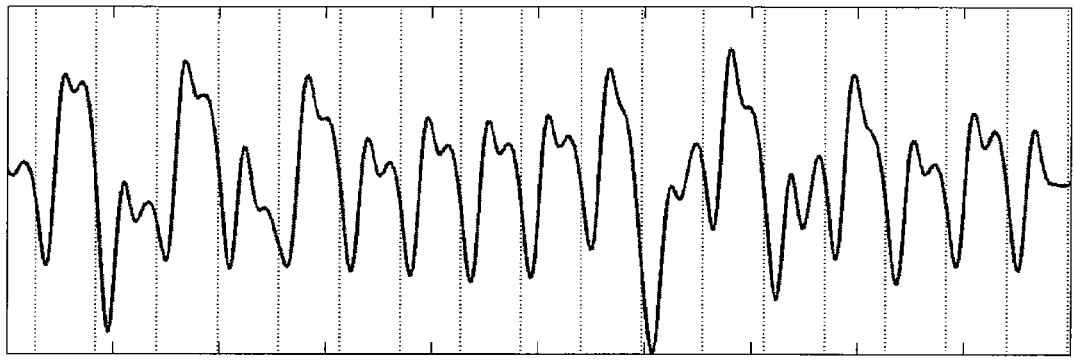
FIG. 7C is the same as FIG. 7B, but with R-wave markers added as vertical dashed lines.
Figure 7D:
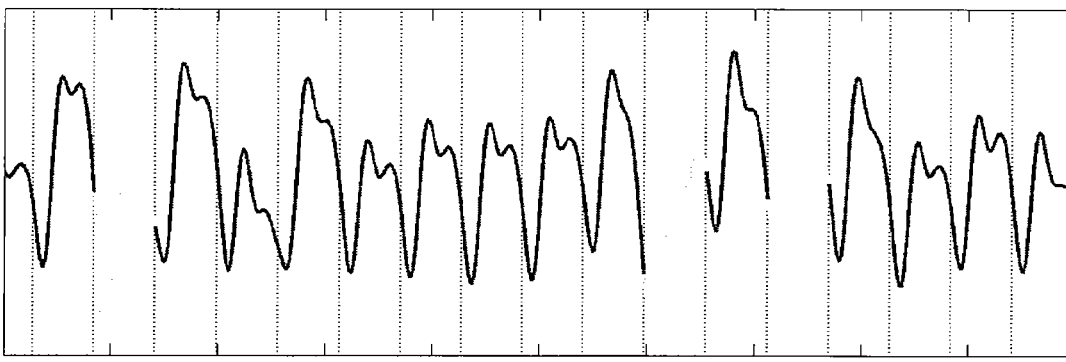
FIG. 7D is similar to FIG. 7C, but shows the removal of three outlier beats.

At step 606, an outlier removal process is performed, to remove "bad" heart beats. In an embodiment, the outlier removal can be accomplished by grouping a plurality (e.g., 20) consecutive heart beats, determining a mean of the filtered PPG signal for the plurality of heart beats, and then comparing the determined mean to individual cycles of the filtered PPG signal. Further, outlier removal can be performed by removing each cardiac cycle of the filtered PPG signal that deviates by at least a threshold amount (e.g., 3 or some other number of standard deviations) from the mean of the PPG signal for the plurality of consecutive beats. FIG. 7C show the filtered signal of FIG. 7B with R-wave markers added (shows as dashed vertical lines). FIG. 7D shows the filtered signal of FIGS. 7B and 7C with 3 "bad" beats removed as a result of an outlier removal process.

Figure 7E:
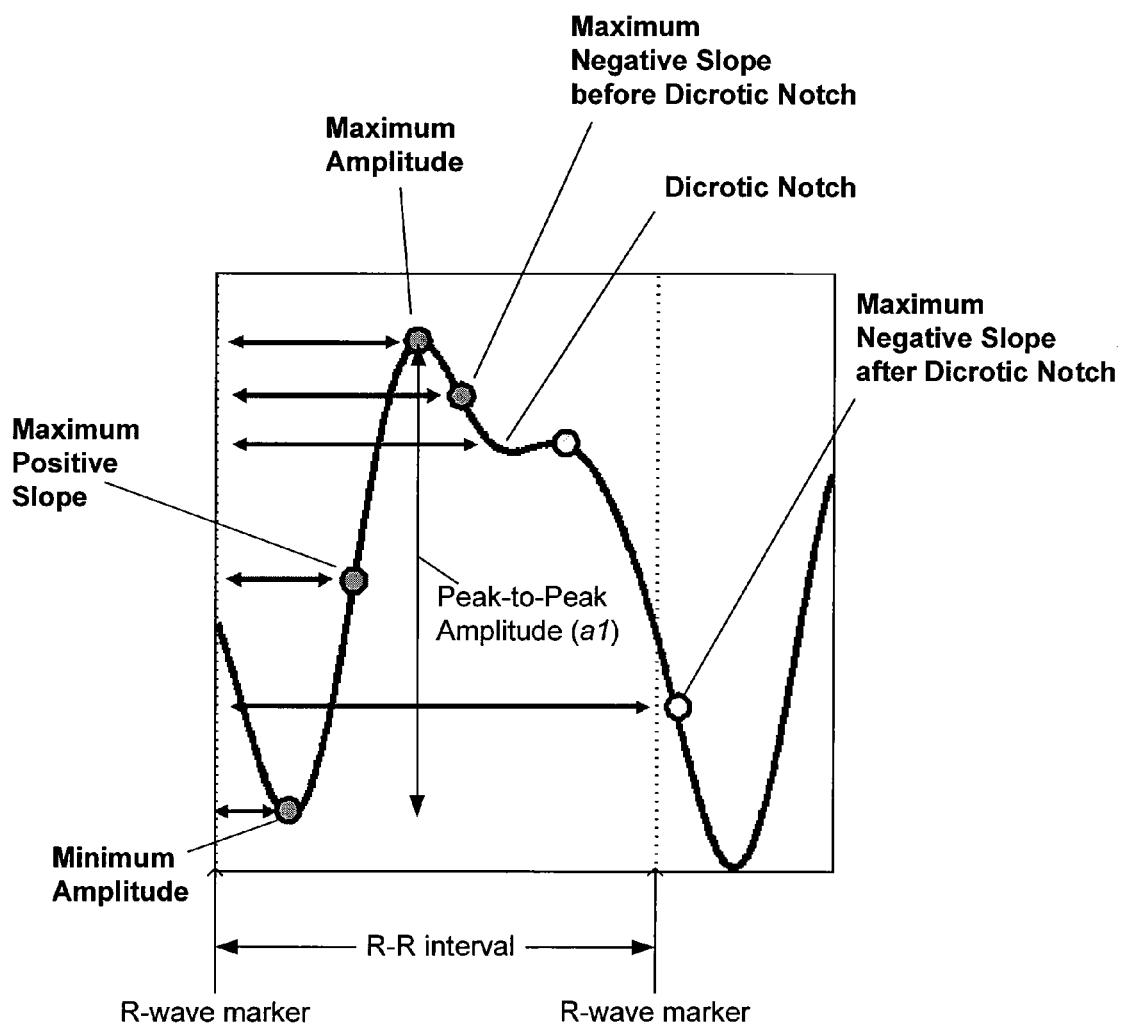
FIG. 7E illustrates an averaged PPG signal resulting from ensemble averaging the remaining cycles of FIG. 7D, and illustrates various feature of the PPG signal that can be determined and used with embodiments of the present invention.

Still referring to FIG. 6, at step 608, the cycles of the PPG signal remaining after the outlier removal step are then ensemble averaged. The result is an average representation of the PPG signal for the plurality of consecutive beats, with noise and "bad" beats removed. FIG. 7E shows an exemplary ensemble averaged PPG signal.

Thereafter, features of the PPG signal can be detected from the ensemble-averaged PPG signal. For example, as indicated at steps 610 and 612, the first derivative of the ensemble-averaged PPG signal can be determined, and the location of the maximum positive slope of the ensemble-averaged PPG signal can be detected by determining the maximum of the first derivative. Further, since it is believed that the maximum positive slope cannot be more than 70% of an R-R interval away from an R-wave, if the location of the maximum positive slope is not within 70% of an R-R interval away from an R wave, a maximum positive slope detection can be determined to be bad, and not be used.

As indicated at steps 614 and 616, the second derivative of the ensemble averaged PPG signal can be determined to find local minima and maxima. The locations of a maximum and a minimum are where the first derivative is equal to zero. The second derivative can be used to determine if a specific location is a maximum or a minimum. More specifically, if the second derivative is positive, then the point is at a minimum. If the second derivative is negative at a point, then the point is a maximum. The local minimum and local maximum that are closest to the maximum positive slope are the minimum and maximum amplitudes of the signal, which can be used, e.g., to determine the peak-to-peak amplitude of the ensemble averaged PPG signal. Further, as indicated at step 618, the maximum negative slope can be determined by identifying, from the first derivative, the local maximum that occurs after the maximum of the averaged PPG signal, but before the subsequent R-wave. As indicated at step 620, from the second derivative, the dicrotic notch can be identified by identifying the local minimum following the maximum of the averaged PPG signal, but before the subsequent R-wave. FIG. 7E shows examples of various predetermined features that can be detected. As shown in FIG. 7E a maximum downward slope can be detected prior to the dicrotic notch, as well as after the dicrotic notch.

Alternative techniques for detecting predetermined features of a PPG signal (or IPG signal) can be used, such as, but not limited to, techniques that rely on template matching, wavelets, neural networks, Fast Fourier Transform (FFT) and/or time warping. Alternatively, or additionally, techniques for detecting predetermined features of a PPG signal (or IPG signal) can utilize respiratory cycles and R-R intervals.

In certain embodiments, since the presence of the dicrotic notch comes and goes under different conditions, monitoring such conditions can use the presence of the dicrotic notch as a binary feature.

Metrics indicative of morphological features of the PPG signal can also be determined based on the ensemble-averaged PPG signal. Such metrics can include, but are not limited to, area under the curve, full width at half max (FWHM), and as already mentioned above, peak-to-peak amplitude ($a_1$ shown in FIGS. 1A, 1B and 7E). As explained above, such morphological features may also be used when determining estimates of arterial blood pressure.

Embodiments of the present invention have been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 2A-2C. Further, it is possible to change the order of some of the steps shown in FIGS. 2A-2C, without substantially changing the overall events and results. For another example, it is possible to change the boundaries of some of the blocks shown in FIG. 4.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. For use with an implantable system, a method for monitoring a patient's arterial blood pressure, the method comprising:
   (a) producing a ventricular pacing signal, which includes a plurality of ventricular pacing pulses, and pacing a patient's heart using the ventricular pacing signal and at least one electrode implanted within or on the patient's heart;
   (b) using an implanted sensor or implanted electrodes, remote from the patient's heart, to obtain a signal indicative of changes in arterial blood volume remote from the patient's heart while the patient's heart is being paced;
   (c) detecting one or more predetermined features of the signal indicative of changes in arterial blood volume remote from the patient's heart obtained at step (b);
   (d) determining one or more metrics indicative of pulse arrival time (PAT), by determining a time from a ventricular pacing pulse of the ventricular pacing signal to one or more of the predetermined features of the signal indicative of changes in arterial blood volume remote from the patient's heart detected at step (c); and
   (e) estimating the patient's arterial blood pressure based on at least one of the one or more metrics indicative of PAT.

2. The method of claim 1, further comprising:
   determining a value indicative of electromechanical delay (EMD) between delivery of pacing at step (a) and a mechanical cardiac contraction resulting from the pacing; and
   wherein step (d) comprises determining at least one of the one or more metrics indicative of PAT also based on the value indicative of EMD.

3. The method of claim 2, wherein step (d) comprises determining at least one of the metrics indicative of PAT by determining a time from a ventricular pacing pulse of the ventricular pacing signal to a predetermined feature of the signal indicative of changes in arterial blood volume remote from the patient's heart, detected at step (c), minus the determined value indicative of EMD.

4. The method of claim 2, further comprising adjusting the pacing at step (a) to reduce variance of the value indicative of electromechanical delay (EMD).

5. The method of claim 1, wherein the signal indicative of changes in arterial blood volume remote from the patient's heart obtained at step (b) comprises a photoplethysmography (PPG) signal or an impedance plethysmography (IPG) signal, and the one or more predetermined features of the PPG or IPG signal detected at step (d) is/are selected from the group consisting of:
   minimum amplitude of the PPG or IPG signal;
   maximum upward slope of the PPG or IPG signal;
   maximum amplitude of the PPG or IPG signal;
   dicrotic notch of the PPG signal or IPG;
   maximum downward slope of the PPG or IPG signal prior to the dicrotic notch; and
   maximum downward slope of the PPG or IPG signal following the dicrotic notch.

6. The method of claim 5, wherein step (d) includes:
   filtering the PPG or IPG signal to reduce effects of respiratory noise, motion artifacts and baseline drift;
   grouping a plurality of cycles of the PPG or IPG signal together and performing an outlier removal process to remove cycles of the PPG or IPG signal that are more than a specified threshold away from the mean of the plurality of cycles of the PPG or IPG signal;
   averaging the cycles of PPG or IPG signal remaining after the performance of the outlier removal process to thereby determine an averaged PPG or IPG signal;
   determining a first derivative and a second derivative of the averaged PPG or IPG signal; and
   detecting, based on the first and second derivatives of the averaged PPG or IPG signal, the one or more predetermined features of the PPG or IPG signal.

7. The method of claim 1, wherein step (e) comprises estimating the patient's arterial blood pressure by determining one or more value selected from the group consisting of:
- a value indicative of systolic blood pressure (SBP) based on at least one of the one or more metrics indicative of PAT;
- a value indicative of diastolic blood pressure (DBP) based on at least one of the one or more metrics indicative of PAT;
- a value indicative of pulse pressure (PP) based on at least one of the one or more metrics indicative of PAT; and
- a value indicative of mean arterial blood pressure (MAP) based on at least one of the one or more metrics indicative of PAT.

8. An implantable system, comprising:
- a pulse generator configured to produce a ventricular pacing signal including a plurality of ventricular pacing pulses that are deliverable to a patient's heart using at least one electrode implanted within or on the patient's heart;
- a plethysmography sensor configured to obtain a signal indicative of changes in arterial blood volume remote from the patient's heart while the patient's heart is being paced with the voltage sufficient to cause capture;
- an arterial blood pressure monitor configured to
  - detect one or more predetermined features of the signal indicative of changes in arterial blood volume remote from the patient's heart;
  - determine one or more metrics indicative of pulse arrival time (PAT) based on times of a ventricular pacing pulse of the ventricular pacing signal and at least one of the one or more detected predetermined features of the signal indicative of changes in arterial blood volume remote from the patient's heart; and
  - estimate the patient's arterial blood pressure based on at least one of the one or more metrics indicative of PAT.

9. The implantable system of claim 8, wherein the implantable plethysmography sensor is selected from the group consisting of:
- a photoplethysmography sensor, remote from the patient's heart, configured to obtain a photoplethysmography (PPG) signal indicative of changes in arterial blood volume remote from the patient's heart; and
- circuitry configured to obtain, using electrodes implanted remote from the patient's heart, an impedance plethysmography signal (IPG) indicative of changes in arterial blood volume remote from the patient's heart.

10. The implantable system of claim 8, wherein the arterial blood pressure monitor is configured to estimate the patient's arterial blood pressure by determining one or more value selected from the group consisting of:
- a value indicative of systolic blood pressure (SBP) based on at least one of the one or more metrics indicative of PAT;
- a value indicative of diastolic blood pressure (DBP) based on at least one of the one or more metrics indicative of PAT;
- a value indicative of pulse pressure (PP) based on at least one of the one or more metrics indicative of PAT; and
- a value indicative of mean arterial blood pressure (MAP) based on at least one of the one or more metrics indicative of PAT.

11. The implantable system of claim 8, wherein the signal indicative of changes in arterial blood volume remote from the patient's heart comprises a photoplethysmography (PPG) signal or an impedance plethysmography (IPG) signal, and wherein the arterial blood pressure monitor is configured to detect one or more predetermined features of the PPG or IPG signal selected from the group consisting of:
- minimum amplitude of the PPG or IPG signal;
- maximum upward slope of the PPG or IPG signal;
- maximum amplitude of the PPG or IPG signal;
- dicrotic notch of the PPG signal or IPG;
- maximum downward slope of the PPG or IPG signal prior to the dicrotic notch; and
- maximum downward slope of the PPG or IPG signal following the dicrotic notch.

12. The implantable system of claim 8, further comprising:
- an electromechanical delay (EMD) monitor configured to determine a value indicative of EMD between delivery of pacing and a mechanical cardiac contraction resulting from the pacing.

13. The implantable system of claim 12, wherein the arterial blood pressure monitor is also configured to determine at least one of the one or more metrics indicative of PAT also based on the value indicative of EMD.

14. The implantable system of 13, wherein the arterial blood pressure monitor is configured to determine at least one of the metrics indicative of PAT by determining a time from a ventricular pacing pulse of the ventricular pacing signal to a detected predetermined feature of the signal indicative of changes in arterial blood volume remote from the patient's heart, minus the determined value indicative of EMD.

15. The implantable system of claim 12, further comprising a controller configured to adjust the pacing to reduce variance of the value indicative of electromechanical delay (EMD).

16. For use with an implantable system, a method for monitoring a patient's arterial blood pressure, the method comprising:
- (a) pacing a patient's heart using a ventricular pacing pulse of a ventricular pacing signal;
- (b) obtaining a photoplethysmography (PPG) signal or an impedance plethysmography (IPG) signal indicative of changes in arterial blood volume remote from the patient's heart while the patient's heart is being paced;
- (c) detecting one or more predetermined features of the PPG or IPG signal indicative of changes in arterial blood volume remote from the patient's heart obtained at step (b);
- (d) determining one or more metrics indicative of pulse arrival time (PAT), by determining a time from a ventricular pacing pulse of the ventricular pacing signal to one or more of the predetermined features of the PPG or IPG signal indicative of changes in arterial blood volume remote from the patient's heart detected at step (c); and
- (e) estimating the patient's arterial blood pressure based on at least one of the one or more metrics indicative of PAT.

* * * * *